(12) United States Patent
Cheung et al.

(10) Patent No.: US 9,637,780 B2
(45) Date of Patent: May 2, 2017

(54) CONTROLLED INHIBITION AND RE-ACTIVATION OF DNA POLYMERASES BY CLEAVABLE OLIGONUCLEOTIDE INHIBITORS

(71) Applicant: HANWHA TECHWIN CO.,LTD., Changwon-si (KR)

(72) Inventors: Win D. Cheung, Olney, MD (US); Jason A. Opdyke, Silver Spring, MD (US)

(73) Assignee: Hanwha Techwin Co., Ltd., Changwon-si (KR)

( * ) Notice: Subject to any disclaimer, the term of this patent is extended or adjusted under 35 U.S.C. 154(b) by 0 days.

(21) Appl. No.: 13/914,745

(22) Filed: Jun. 11, 2013

(65) Prior Publication Data

US 2013/0330734 A1 Dec. 12, 2013

Related U.S. Application Data

(60) Provisional application No. 61/658,212, filed on Jun. 11, 2012.

(51) Int. Cl.
  *C12Q 1/68* (2006.01)
  *C12P 19/34* (2006.01)

(52) U.S. Cl.
  CPC ........... *C12Q 1/686* (2013.01); *C12Q 1/6848* (2013.01)

(58) Field of Classification Search
  None
  See application file for complete search history.

(56) References Cited

U.S. PATENT DOCUMENTS

| | | | |
|---|---|---|---|
| 6,183,967 B1* | 2/2001 | Jayasena et al. | 435/5 |
| 6,830,902 B1* | 12/2004 | Astatke | C12Q 1/6844 435/7.1 |
| 2013/0288245 A1* | 10/2013 | Walder et al. | 435/6.11 |

* cited by examiner

*Primary Examiner* — David Thomas
(74) *Attorney, Agent, or Firm* — Sughrue Mion, PLLC

(57) ABSTRACT

A hot start enzyme composition is described that includes a hot start nuclease, a nucleic acid polymerase, and a substantially double-stranded oligonucleotide that inhibits the catalytic activity of the nucleic acid polymerase at temperatures lower than the melting temperature of the oligonucleotide.

15 Claims, 6 Drawing Sheets

Fig. 6

```
                                        *        20         *        40         *
Haemophilus_influenzae    : MFNLSLSIKIPATLHNNLFVMQKQIRIFTDGCCGNPCAGGTAVLRYKQ :  50
Thermus_thermophilus      : ------------------MNPSPEKRVALFTDGACGNPCGGAALLRPHA :  34
Thermus_aquaticus         : -------------------MS-LSLERVGLFTDGACGNPCGGAALLRYGS :  33
Salmonella_enterica       : --------------------MIRCVEIFTDGCCGNPCGGAILRYRG :  30
Agrobacterium_tumefaciens : ---------------------MRHVDIPTDGACGNPCGGAVLRYGS :  29
                                              K  G  GFTDG C GNPCpGG    A6LR5

*        60         *        80         *       100
Haemophilus_influenzae    : HEKMISKEYFATTNNRMELRAVDEALTLKHCLRITDSDSGYMRNGIRK : 100
Thermus_thermophilus      : REKLLSEGEAQTTNNRMELAAIEGLKLKHCVLLTDSHYLKRAFER :  84
Thermus_aquaticus         : QRKLLSEGRPTTNNRMELAAIEGLLLKWHCVLLTDSHYLKRAFAR :  83
Salmonella_enterica       : RERTFSEGYTLTTNNRMELAAIVALELKHCVPLTDSYVRQRIKQ :  80
Agrobacterium_tumefaciens : TEKELSKGEADTTNNRMELLASADLKSCCVLLTDSAYVERGIRK :  79
                              EK  S G    TTNNRMEL Aa     L aLdepC  6  L 3DS Y64       t

*       120         *       140         *
Haemophilus_influenzae    : -RIFNNIKHWKASSGKPVKNILWNLDESQPHITNQDVGHGHGHES : 149
Thermus_thermophilus      : GELEGWIKYIARDESKPVKNILWIALLAPRYVIRYGHGHGHE : 134
Thermus_aquaticus         : GWERMDRILVRERSKPVKNILWIILKEPRVAHEVGHGHGHE : 133
Salmonella_enterica       : -MIDNMIKFIERNEKPVKNVELNCRIDALSERIVWVGHAGHE : 129
Agrobacterium_tumefaciens : -MIFGMIKVIKQDNKPVKNVELNCLEAQSPHITLNTVGHGHE : 128
                              WG  W  4  g##ta   KPVKN  dLW  aL   a     H  6    GVKGH GHpE

*       160         *       180
Haemophilus_influenzae    : NELCDELAKIGNENPTLEDNGYFEE-------- : 174 (SEQ ID NO:16)
Thermus_thermophilus      : NELVLREARLQQSQAKTPCPPRAPTLFHEEA   : 166 (SEQ ID NO:15)
Thermus_aquaticus         : NELVLREARLKAQPQVPCPDKEATLF----    : 161 (SEQ ID NO:14)
Salmonella_enterica       : NELCRELAAMNNETQ-------------      : 145 (SEQ ID NO:18)
Agrobacterium_tumefaciens : NELADELARKMEPFKRR--------------   : 145 (SEQ ID NO:19)
                             NEL  D   A#     a
```

_US 9,637,780 B2_

CONTROLLED INHIBITION AND RE-ACTIVATION OF DNA POLYMERASES BY CLEAVABLE OLIGONUCLEOTIDE INHIBITORS

CROSS-REFERENCE TO RELATED APPLICATION

This application is a non-provisional application of U.S. Provisional Application No. 61/658,212 filed Jun. 11, 2012, the contents of all of which are incorporated herein by reference in their entirety.

FIELD

The disclosure describes a hot start PCR composition for the improved real-time PCR detection of target nucleic acid sequences.

BACKGROUND

Among many analytical methods of detecting and quantifying nucleic acids, PCR is one of the most commonly used methods, the principles of which are disclosed in U.S. Pat. Nos. 4,683,195 and 4,683,202. Despite the obvious advantages of the PCR methodology, the ability to amplify low copy DNA template sequences by several orders of magnitude also means that the success of a PCR amplification reaction is determined in large part already during the first PCR cycle, where non-specific priming can result in the amplification of spurious PCR products, such as primer dimers. Once present in the reaction, these non-specific PCR products are amplified along with the targeted DNA sequence thereby compromising the specificity and the overall efficiency of a PCR amplification reaction.

In an effort to suppress non-specific priming, so-called 'hot start' PCR protocols, have been devised in which the polymerase activity is suppressed prior to the initial denaturation of the template and PCR primers during the first PCR cycle. This approach therefore seeks to minimize spurious primer extension at low temperatures that can lead to the formation of primer dimers or other non-specific PCR products. Suppressing polymerase activity at low temperatures is however problematic when the PCR primers themselves anneal specifically to the targeted DNA sequence at low temperatures.

For the foregoing reasons, there is an unmet need in the art for improved hot-start PCR protocols.

SUMMARY

A hot start enzyme composition is described that includes a hot start nuclease and a substantially double-stranded oligonucleotide that inhibits the catalytic activity of a nucleic acid polymerase at temperatures lower than the melting temperature of the oligonucleotide. With the initiation of the denaturation/annealing step of the first PCR amplification cycle, activation of the hot start nuclease inactivates the double-stranded oligonucleotide by endonucleolytic cleavage which, in turn, results in the activation of the nucleic acid polymerase at the elongation step of the first PCR amplification cycle. In real-time PCR applications, an activated hot start RNase H activity is also disclosed that participates in both the hot start activation of the amplifying nucleic acid polymerase during the first cycle of PCR amplification and the subsequent cleavage and fluorescent detection of CATACLEAVE™ probes that anneal to the amplified target nucleic acid sequences. This hot start method is therefore especially suited to high throughput real-time PCR applications.

In one embodiment, the invention includes a hot start enzyme composition including:
a nucleic acid polymerase activity,
a substantially double-stranded oligonucleotide that inhibits the nucleic acid polymerase activity at a temperature lower than the melting temperature of the oligonucleotide, and
a hot start nuclease activity, wherein the activation of the hot start nuclease activity irreversibly abolishes the inhibition of the nucleic acid polymerase activity.

In certain embodiments, the substantially double-stranded oligonucleotide includes at least one RNA:DNA base pair that can be cleaved by the activated hot start nuclease activity.

The nucleic acid polymerase activity can be the activity of a DNA polymerase, an RNA polymerase or a reverse transcriptase or a thermophilic nucleic acid polymerase activity.

The hot start nuclease activity can be the activity of a hot start thermostable RNase H.

The 3'-end and/or 5'-end of the substantially double-stranded oligonucleotide can be chemically modified. Denaturation of the oligonucleotide can produce at least two single-stranded oligonucleotides. In other instances, the substantially double-stranded oligonucleotide has a hairpin loop structure.

In one embodiment, the invention discloses a method of activating a hot start nucleic acid polymerase activity including:
providing a nucleic acid polymerase,
a substantially double-stranded oligonucleotide comprising at least one RNA:DNA base pair, wherein the oligonucleotide inhibits the nucleic acid polymerase activity at a temperature lower than the melting temperature of the oligonucleotide, and
a hot start RNAse H activity, and
activating the hot start composition,
wherein the activated hot start RNAse H activity cleaves the oligonucleotide at the at least one RNA: DNA base pair thereby irreversibly abolishing the ability of the oligonucleotide to inhibit the nucleic acid polymerase.

In another embodiment, a kit having a hot start enzyme composition is disclosed that includes
a nucleic acid polymerase activity,
a substantially double-stranded oligonucleotide that inhibits the nucleic acid polymerase activity at a temperature lower than the melting temperature of the oligonucleotide, and
a hot start nuclease activity,
wherein the activation of the hot start nuclease activity irreversibly abolishes the inhibition of the nucleic acid polymerase activity by the oligonucleotide.

In another embodiment, a method of amplifying a target nucleic acid sequence is described including:
providing a sample to be tested for the presence of a target nucleic acid sequence,
providing a pair of forward and reverse amplification primers, wherein the forward amplification primer anneals to the 5' end of the target nucleic acid sequence and the reverse amplification primer anneals to the 3' end of the target nucleic acid sequence,
providing a hot start enzyme composition including
a nucleic acid polymerase activity,
a substantially double-stranded oligonucleotide that inhibits the nucleic acid polymerase activity at a temperature lower than the melting temperature of the oligonucleotide, and
a hot start nuclease activity,
amplifying a PCR fragment between the forward and reverse amplification primers in the presence of the target DNA sequence, an amplification buffer and the hot start enzyme composition for at least one amplification cycle, wherein the activation of the hot start nuclease activity irreversibly abolishes the inhibition of the nucleic acid polymerase activity by the oligonucleotide during the first amplification cycle.

In another embodiment, a method for the real-time detection of a target DNA sequence in a sample is described that includes:

providing a sample to be tested for the presence of a target DNA sequence, providing a pair of forward and reverse amplification primers, wherein the forward amplification primer anneals to the 5' end of the target nucleic acid sequence and the reverse amplification primer anneals to the 3' end of the target nucleic acid sequence, providing a probe including a detectable label and DNA and RNA nucleic acid sequences, wherein the probe's RNA nucleic acid sequences are substantially complementary to a selected region of the target DNA and the probe's DNA nucleic acid sequences are substantially complementary to sequences adjacent to the selected region of the target DNA sequence, providing a hot start enzyme composition including:
a nucleic acid polymerase activity,
a substantially double-stranded oligonucleotide that inhibits the nucleic acid polymerase activity at a temperature lower than the melting temperature of the oligonucleotide, and
a hot start nuclease activity, wherein the inhibition of the nucleic acid polymerase activity by the oligonucleotide is irreversibly abolished by the activation of the hot start nuclease activity, amplifying a PCR fragment between the forward and reverse amplification primers in the presence of the target DNA sequence, an amplification buffer, the hot start enzyme composition and the probe for at least one amplification cycle under conditions where the substantially double-stranded oligonucleotide is irreversibly inactivated during the first amplification cycle and the RNA sequences within the probe can form a RNA:DNA heteroduplex with complimentary sequences in the PCR fragment; and detecting a real-time increase in the emission of a signal from the label on the probe, wherein the increase in signal indicates the presence of the target nucleic acid sequences in the sample.

In one aspect, the real-time increase in the emission of the signal from the label on the probe results from the RNAse H cleavage of the probe's RNA sequences in the RNA:DNA heteroduplex.

In another aspect, the DNA and RNA sequences of the probe can be covalently linked. The detectable label on the probe can a fluorescent label such as a FRET pair. The PCR fragment or probe can be linked to a solid support.

In another embodiment, the invention describes a method for the real-time detection of an RNA target sequence in a sample, including:

providing a sample to be tested for the presence of a target RNA sequence;

providing a pair of forward and reverse amplification primers, wherein the forward amplification primer anneals to the 5' end of the target nucleic acid sequence and the reverse amplification primer anneals to the 3' end of the target nucleic acid sequence;

providing a probe comprising a detectable label and DNA and RNA nucleic acid sequences, wherein the probe's RNA nucleic acid sequences are substantially complementary to a selected region of a target cDNA sequence and the probe's DNA nucleic acid sequences are substantially complementary to the target DNA sequences adjacent to the selected region of the target cDNA sequence;

providing the hot start enzyme composition including
a nucleic acid polymerase activity,
a substantially double-stranded oligonucleotide that inhibits the
nucleic acid polymerase activity at a temperature lower than the
melting temperature of the oligonucleotide, and
a hot start nuclease activity,
wherein the inhibition of the nucleic acid polymerase activity by the oligonucleotide is irreversibly abolished by the activation of the hot start nuclease activity;

reverse transcribing the target RNA in the presence of a reverse transcriptase activity and the reverse amplification primer to produce the target cDNA sequence;

amplifying an PCR fragment between the forward and reverse amplification primers in the presence of the target cDNA sequence, the hot start enzyme composition, an amplification buffer and the probe for at least one amplification cycle under conditions where the substantially double-stranded oligonucleotide is irreversibly inactivated during the first amplification cycle and the RNA sequences within the probe can form a RNA:DNA heteroduplex with complimentary sequences in the PCR fragment; and detecting a real-time increase in the emission of a signal from the label on the probe, wherein the increase in signal indicates the presence of the target RNA sequence in the sample.

In one aspect, the real-time increase in the emission of the signal from the label on the probe can result from the RNAse H cleavage of the probe's RNA sequences in the RNA: DNA heteroduplex.

In one embodiment, an enzyme composition is disclosed comprising: a nucleic acid polymerase activity, and a substantially double-stranded oligonucleotide, wherein the oligonucleotide inhibits the nucleic acid polymerase activity at a temperature lower than the melting temperature of the oligonucleotide, wherein the inhibition of the nucleic acid polymerase activity by the oligonucleotide is irreversibly abolished by the addition of a nuclease activity.

In another embodiment, a method of amplifying a target nucleic acid sequence is described that includes:

providing a sample to be tested for the presence of a target nucleic acid sequence;

providing a pair of forward and reverse amplification primers, wherein the forward amplification primer anneals to the 5' end of the target nucleic acid sequence and the reverse amplification primer anneals to the 3' end of the target nucleic acid sequence;

providing an enzyme composition having a nucleic acid polymerase activity, and a substantially double-stranded oligonucleotide, wherein the oligonucleotide inhibits the nucleic acid polymerase activity at a temperature lower than the melting temperature of the oligonucleotide, wherein the inhibition of the nucleic acid polymerase activity by the oligonucleotide is irreversibly abolished by the addition of a nuclease activity;

adding the nuclease activity;

amplifying a PCR fragment between the forward and reverse amplification primers in the presence of the target DNA sequence and an amplification buffer, wherein the substantially double-stranded oligonucleotide is irreversibly inactivated by the nuclease activity.

In another embodiment, a method for the real-time detection of a target DNA sequence in a sample is disclosed which comprises:

providing a sample to be tested for the presence of a target DNA sequence;

providing a pair of forward and reverse amplification primers, wherein the forward amplification primer anneals to the 5' end of the target nucleic acid sequence and the reverse amplification primer anneals to the 3' end of the target nucleic acid sequence;

providing a probe comprising a detectable label and DNA and RNA nucleic acid sequences, wherein the probe's RNA nucleic acid sequences are entirely complementary to a selected region of the target DNA and the probe's DNA nucleic acid sequences are substantially complementary to sequences adjacent to the selected region of the target DNA sequence;

providing an enzyme composition having a nucleic acid polymerase activity, and a substantially double-stranded oligonucleotide, wherein the oligonucleotide inhibits the nucleic acid polymerase activity at a temperature lower than the melting temperature of the oligonucleotide, wherein the inhibition of the nucleic acid polymerase activity by the oligonucleotide is irreversibly abolished by the addition of a nuclease activity;

adding the nuclease activity;

amplifying a PCR fragment between the forward and reverse amplification primers in the presence of the target DNA sequence, an amplification buffer, the enzyme composition and the probe for at least one amplification cycle under conditions where the substantially double-stranded oligonucleotide is irreversibly inactivated by the nuclease activity and the RNA sequences within the probe can form a RNA:DNA heteroduplex with complimentary sequences in the PCR fragment; and detecting a real-time increase in the emission of a signal from the label on the probe, wherein the increase in signal indicates the presence of the target DNA sequence in the sample.

In yet another embodiment, a method for the real-time detection of an RNA target sequence in a sample, comprising:

providing a sample to be tested for the presence of a target RNA sequence;

providing a pair of forward and reverse amplification primers, wherein the forward amplification primer anneals to the 5' end of a target nucleic acid sequence and the reverse amplification primer anneals to the 3' end of the target nucleic acid sequence;

providing a probe comprising a detectable label and DNA and RNA nucleic acid sequences, wherein the probe's RNA nucleic acid sequences are entirely complementary to a selected region of a target cDNA sequence and the probe's DNA nucleic acid sequences are substantially complementary to target DNA sequences adjacent to the selected region of the target cDNA sequence;

providing an enzyme composition having a nucleic acid polymerase activity, and a substantially double-stranded oligonucleotide, wherein the oligonucleotide inhibits the nucleic acid polymerase activity at a temperature lower than the melting temperature of the oligonucleotide, wherein the inhibition of the nucleic acid polymerase activity by the oligonucleotide is irreversibly abolished by the addition of a nuclease activity;

reverse transcribing the target RNA in the presence of a reverse transcriptase activity and the reverse amplification primer to produce the target cDNA sequence;

adding the nuclease activity;

amplifying an PCR fragment between the forward and reverse amplification primers in the presence of the target cDNA sequence, the enzyme composition, an amplification buffer and the probe for at least one amplification cycle under conditions where the substantially double-stranded oligonucleotide is irreversibly inactivated by the nuclease activity and the RNA sequences within the probe can form a RNA:DNA heteroduplex with complimentary sequences in the PCR fragment; and detecting a real-time increase in the emission of a signal from the label on the probe, wherein the increase in signal indicates the presence of the target RNA sequences in the sample.

The previously described embodiments have many advantages, including the ability to inhibit the catalytic activity of a nucleic acid polymerase prior to the initiation of PCR amplification. Moreover, the sensitivity and specificity of the PCR amplification is further enhanced by abolishing this inhibition of the nucleic acid polymerase after the first cycle of PCR amplification.

In certain embodiments, an activated hot start RNase H activity participates in the hot start activation of the amplifying nucleic acid polymerase during the first cycle of PCR amplification and, subsequently, promotes the cleavage and fluorescent detection of CATACLEAVE™ probes that anneal to target nucleic acid sequences during real-time PCR application. The hot start method is therefore especially suited to high throughput real time PCR applications.

BRIEF DESCRIPTION OF THE DRAWINGS

The skilled artisan will understand that the drawings, described below, are for illustration purposes only. The figures are not intended to limit the scope of the teachings in any way.

FIG. 6 depicts sequence alignment of *Haemophilus influenzae* (SEQ ID NO: 26), *Thermus thermophilis* (SEQ ID NO: 15), *Thermus acquaticus* (SEQ ID NO: 27), *Salmonella enterica* (SEQ ID NO: 28) and *Agrobacterium tumefaciens* (SEQ ID NO: 29) RNase HI polypeptide sequences.

DETAILED DESCRIPTION

Figure 1:
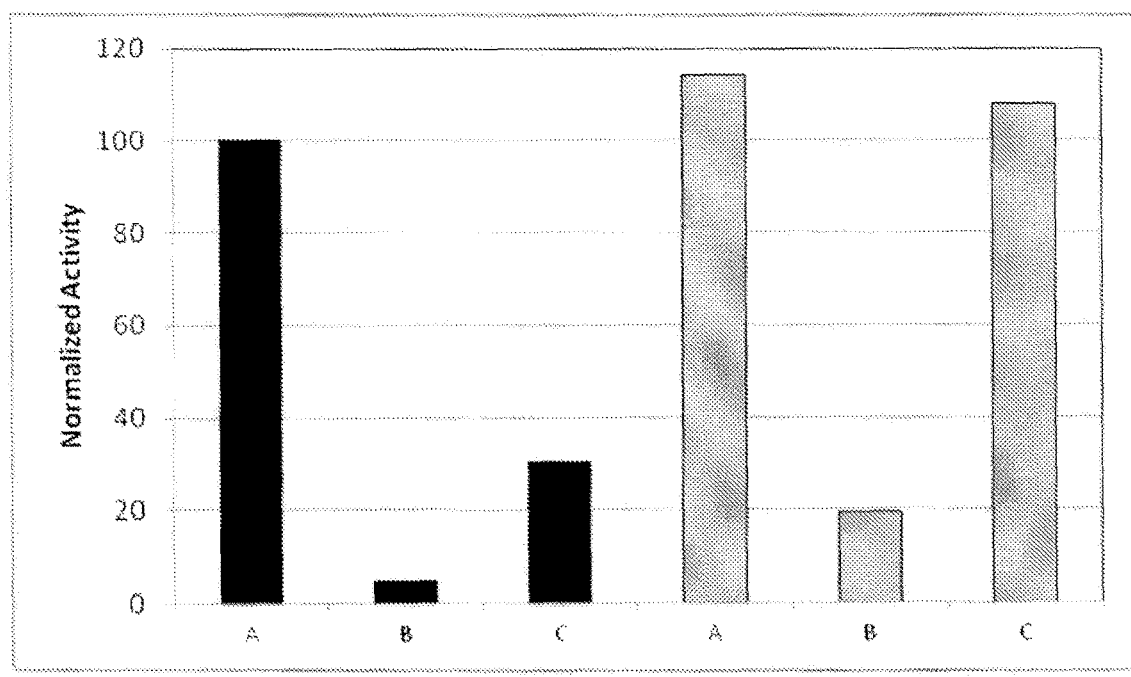
FIG. 1 depicts the efficiency of PCR amplification tested in the absence of HotStart RNase HII (black bars) or the presence of HotStart RNase HII (gray bars) and in the presence of Taq Polymerase (A), Taq Polymerase+T-Pin 1 (SEQ ID NO: 2) (B) or Taq Polymerase+T-Pin 4 (SEQ ID NO: 3) (C). T-Pin 4 (SEQ ID NO: 3) is cleavable by HotStart RNase HII whereas T-Pin 1 (SEQ ID NO: 2) is not.

The practice of the invention employs, unless otherwise indicated, conventional molecular biological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements; Sambrook, et al., Molecular Cloning: A Laboratory Manual, 2nd Edition, Cold Spring Harbor, N.Y. (1989).

Unless defined otherwise, all technical and scientific terms used herein have the same meaning as is commonly understood by one of skill in the art. The specification also provides definitions of terms to help interpret the disclosure and claims of this application. In the event a definition is not consistent with definitions elsewhere, the definition set forth in this application will control.

As used herein, the term "base" refers to any nitrogen-containing heterocyclic moiety capable of forming Watson-Crick type hydrogen bonds in pairing with a complementary base or base analog. A large number of natural and synthetic (non-natural, or unnatural) bases, base analogs and base derivatives are known. Examples of bases include purines, pyrimidines, and modified forms thereof. The naturally occurring bases include, but are not limited to, adenine (A), guanine (G), cytosine (C), uracil (U) and thymine (T). As used herein, it is not intended that the invention be limited to naturally occurring bases, as a large number of unnatural (non-naturally occurring) bases and their respective unnatural nucleotides that find use with the invention are known to one of skill in the art.

The term "nucleoside" refers to a compound consisting of a base linked to the C-1' carbon of a sugar, for example, ribose or deoxyribose.

The term "nucleotide" refers to a phosphate ester of a nucleoside, as a monomer unit or within a polynucleotide. The term "nucleotide," as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR2 or halogen groups, where each R is independently H, C1-C6 alkyl or C5-C14 aryl. Exemplary riboses include, but are not limited to, 2'-(C1-C6)alkoxyribose, 2'-(C5-C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose, ribose, 2'-deoxyribose, 2',3'-dideoxyribose, 2'-haloribose, 2'-fluororibose, 2'-chlororibose, and 2'-alkyl-ribose, e.g., 2'-O-methyl, 4'-α-anomeric nucleotides, 1'-α-anomeric nucleotides, 2'-4'- and 3'-4'-linked and other "locked" or "LNA", bicyclic sugar modifications (see, e.g., PCT published application nos. WO 98/22489, WO 98/39352, and WO 99/14226; and U.S. Pat. Nos. 6,268,490 and 6,794,499). Further synthetic nucleotides having modified base moieties and/or modified sugar moieties, e.g., as described by Scheit: Nucleotide Analogs (John Wiley New York, 1980); Uhlman and Peyman, 1990, Chemical Reviews 90:543-584.

The terms "polynucleotide," "nucleic acid," "oligonucleotide," "oligomer," "oligo," primer or equivalent terms, as used herein refer to a polymeric arrangement of monomers that can be corresponded to a sequence of nucleotide bases, such as deoxyribonucleic acid (DNA), ribonucleic acid (RNA), and, where appropriate, phosphothioate containing nucleic acids, locked nucleic acid (LNA), peptide nucleic acid (PNA), or other derivative nucleic acid molecules and combinations thereof.

Nucleic acids include, but are not limited to, synthetic DNA, plasmid DNA, genomic DNA, cDNA, hnRNA, small nuclear snRNA, mRNA, rRNA, tRNA, miRNAs, fragmented nucleic acid, nucleic acid obtained from subcellular organelles such as mitochondria or chloroplasts, and nucleic acid obtained from microorganisms or DNA or RNA viruses that may be present on or in a biological sample. Nucleic acids may be composed of a single type of sugar moiety, e.g., as in the case of RNA and DNA, or mixtures of different sugar moieties, e.g., as in the case of RNA/DNA chimeras.

Polynucleotides are polymers of nucleotides comprising two or more nucleotides. Polynucleotides may be double-stranded nucleic acids, including annealed oligonucleotides wherein the second strand is an oligonucleotide with the reverse complement sequence of the first oligonucleotide, single-stranded nucleic acid polymers comprising deoxythymidine, single-stranded RNAs, double stranded RNAs or RNA/DNA heteroduplexes or single-stranded nucleic acid polymers comprising double stranded regions e.g. DNA hairpin loops and/or RNA hairpin loops and/or DNA/RNA hairpin loops.

As used herein, an "oligonucleotide" refers to a short polynucleotide. In certain embodiments, an oligonucleotide may be about 10, about 20, about 30, about 40, about 50 or more 60 nucleotides in length. In other embodiments, an oligonucleotide is less than about 500 nucleotides, less than about 250 nucleotides, less than about 200 nucleotides, less than about 150 nucleotide or less than 100 nucleotides.

Oligonucleotides or polynucleotides may be modified or may comprise modified bases or modified or non-naturally occurring sugar residues. Several reviews on modified oligonucleotides, including conjugates have been published; see for example, Verma and Eckstein Annu. Rev. Biochem. (1998) 67:99-134, Uhlmann and Peyman, Chemical Reviews, Vol. 90, pgs. 543-584 (1990), and Goodchild, Bioconjugate Chemistry, Vol. 1, pgs 165-187 (1990), Cobb Org Biomol Chem. (2007) 5(20):3260-75, Lyer et al. Curr Opin Mol. Ther. (1999) 1(3):344-58), U.S. Pat. Nos. 6,172, 208, 5,872,244 and published U.S. Patent Application No. 2007/0281308.

The term "template nucleic acid" refers to a plurality of nucleic acid molecules used as the starting material or template for amplification in a PCR reaction or reverse transcriptase-PCR reaction. Template nucleic acid sequences may include both naturally occurring and synthetic molecules. Exemplary template nucleic acid sequences include, but are not limited to, genomic DNA or genomic RNA.

A "target DNA" or "target RNA" or "target nucleic acid," or "target nucleic acid sequence" refers to a region of a template nucleic acid that is to be analyzed.

As used herein, the term "amplification primer" or "PCR primer" or "primer" refers to an enzymatically extendable oligonucleotide that comprises a defined sequence that is designed to hybridize in an antiparallel manner with a complementary, primer-specific portion of a target nucleic acid sequence. Thus, the primer, which is generally in molar excess relative to its target polynucleotide sequence, primes template-dependent enzymatic DNA synthesis and amplification of the target sequence. A primer nucleic acid does not need to have 100% complementarity with its template subsequence for primer elongation to occur; primers with less than 100% complementarity can be sufficient for hybridization and polymerase elongation to occur provided the penultimate base at the 3' end of the primer is able to base pair with the template nucleic acid. A PCR primer is preferably, but not necessarily, synthetic, and will generally be approximately about 10 to about 100 nucleotides in length.

Oligonucleotides may be synthesized and prepared by any suitable method (such as chemical synthesis), which is known in the art. A number of computer programs (e.g., Primer-Express) are readily available to design optimal primer sets. One of the skilled artisans would therefore easily optimize and identify primers flanking a target nucleic acid sequence of interest. For example, synthesized primers can be between 20 and 26 base pairs in length with a melting point ($T_M$) of around 55 degrees. Commercially available primers may also be used to amplify a particular target nucleic acid sequence of interest. Hence, it will be apparent to one of skill in the art that the primers and probes based on the nucleic acid information provided (or publicly available with accession numbers) can be prepared accordingly.

The terms "annealing" and "hybridization" are used interchangeably and mean the base-pairing interaction of one nucleic acid with another nucleic acid that results in formation of a duplex, triplex, or other higher-ordered structure. In certain embodiments, the primary interaction is base-specific, e.g., A/T and G/C, by Watson/Crick and Hoogsteen-type hydrogen bonding. In certain embodiments, base-stacking and hydrophobic interactions may also contribute to duplex stability. "Substantially complimentary" refers to two nucleic acid strands that are sufficiently complimentary in sequence to anneal and form a stable duplex.

Nucleic Acid Template Preparation

Nucleic acid templates can be derived from humans, non-human animals, plants, bacteria, fungi, protozoa, viruses and recombinant nucleic acids such as plasmid, phage or viral vectors.

In certain embodiments, the template nucleic acid is purified from a sample which may comprise prokaryotic or eukaryotic cells, cultured cells, human or animal fluid or tissues including, but not limited to, blood, saliva, sputum, urine, feces, skin cells, hair follicles, semen, vaginal fluid, bone fragments, bone marrow, brain matter, cerebrospinal fluid, amniotic fluid, and the like. Samples may also include bacterial cells or spores (including gram+ or gram−), and viruses (including DNA-based and RNA-based). In some embodiments, the samples may be collected using swab sampling of surfaces.

Procedures for the extraction and purification of nucleic acids from samples are well known in the art (as described in Sambrook J et. al. Molecular Cloning, Cold Spring harbor Laboratory Press (1989), Ausubel et al. Short Protocols in Molecular Biology, 5th Ed. (2002) John Wiley & Sons, Inc. New York).

In addition, several commercial kits are available for the isolation of nucleic acids. Exemplary kits include, but are not limited to, Puregene DNA isolation kit (PG) (Gentra Systems, Inc., Minneapolis, Minn.), Generation Capture Column kit (GCC) (Gentra Systems, Inc.), MasterPure DNA purification kit (MP) (Epicentre Technologies, Madison, Wis.), Isoquick nucleic acid extraction kit (IQ) (Epoch Pharmaceuticals, Bothell, Wash.), NucliSens isolation kit (NS) (Organon Teknika Corp., Durham, N.C.), QIAamp DNA Blood Mini Kit (Qiagen; Cat. No. 51104), MagNA Pure Compact Nucleic Acid Isolation Kit (Roche Applied Sciences; Cat. No. 03730964001), Stabilized Blood-to-CT™ Nucleic Acid Preparation Kit for qPCR (Invitrogen, Cat. No. 4449080) and GF-1 Viral Nucleic Acid Extraction Kit (GeneOn, Cat. No. RD05).

Hot Start Enzyme Composition

The invention discloses a hot start composition including a nucleic acid polymerase, a hot start nuclease and a substantially double-stranded oligonucleotide that inhibits the catalytic activity of the nucleic acid polymerase at a temperature lower than its melting temperature. In a preferred embodiment, the substantially double stranded oligonucleotide comprises at least one RNA:DNA base pair that is cleavable with a hot start RNase H and the 3' end of the oligonucleotide is modified to prohibit primer extension.

The hot start procedure operates as follows. At room temperature, or a temperature below the melting temperature of the oligonucleotide, the oligonucleotide adopts a substantially double-stranded structure that is thought to bind to the active site of the nucleic acid polymerase and inhibits the catalytic activity of the nucleic acid polymerase.

With the initiation of the first cycle of PCR, the PCR reaction is first heated to a temperature of about 95° C. that (1) releases the oligonucleotide from the polymerase and denatures it and (2) activates the hot start RNase H. Cooling of the PCR reaction to a temperature approaching the annealing temperature of the oligonucleotide then ensues at which point the re-annealed at least one RNA:DNA base pair within the oligonucleotide is immediately cleaved by the activated hot start RNase H. The location of the at least one RNA:DNA base pair in the oligonucleotide is designed in such a way that the cleavage of the re-annealed substantially double-stranded oligonucleotide by the hot start RNase H produces fragments having a Tm that is well below the temperature of the PCR reaction's annealing step. Thus, at temperatures found in subsequent PCR cycles that are always kept at or above the PCR reaction's annealing temperature, the oligonucleotide fragments remain single-stranded and therefore unable to interfere with or otherwise inhibit the catalytic activity of the now activated nucleic acid polymerase.

One advantage this hot start composition has over traditional antibody-based hot start compositions is that a single oligonucleotide inhibitor can inhibit DNA polymerases from all organisms, while different antibodies would be required to inhibit DNA polymerases from different organisms.

Another major advantage this hot start composition has over other oligonucleotide inhibitors is the fact that it is irreversible. The reversible nature of other conventional oligonucleotide inhibitors limits extension temperature of the PCR to be around the Tm of the oligonucleotide inhibitor. There is actually a substantial amount of polymerization that occurs during the annealing step (which may be below the Tm of the inhibitor), and the use of conventional oligonucleotide inhibitors inhibits polymerization during the annealing step. With the instant hot start composition, the Tm of the oligonucleotide inhibitor is not limited to be 50-55 C, and may be much higher.

Each of the components of the hot start composition is now described in detail.

The Nucleic Acid Polymerase

The nucleic acid polymerase can have one or more of the activities of a DNA-dependent DNA polymerase, a DNA-dependent RNA polymerase, a RNA-dependent DNA polymerase or a RNA dependent RNA polymerase.

A "DNA-dependent DNA polymerase activity" refers to the activity of a DNA polymerase enzyme that uses deoxyribonucleic acid (DNA) as a template for the synthesis of a complementary and anti-parallel DNA strand (see below).

A "DNA-dependent RNA polymerase activity" refers to the activity of an RNA polymerase enzyme that uses deoxyribonucleic acid (DNA) as a template for the synthesis of an RNA strand in a process called "transcription." (for example, Thermo T7 RNA polymerase, commercially available from Toyobo Life Science Department, Catalogue No. TRL-201)

A "RNA-dependent DNA polymerase activity" refers to the activity of a DNA polymerase enzyme that uses ribonucleic acid (RNA) as a template for the synthesis of a complementary and anti-parallel DNA strand in a process called "reverse transcription." (see below)

A "RNA-dependent RNA polymerase activity" refers to the activity of a RNA polymerase enzyme that uses ribonucleic acid (RNA) as a template for the synthesis of a complementary RNA strand (for example, *Thermus thermophilus* RNA polymerase, commercially available from Cambio, Catalogue No. T90250).

In certain embodiments, the nucleic acid polymerase is a thermostable polymerase that may have more than one of the above-specified catalytic activities.

As used herein, the term "thermostable," as applied to an enzyme, refers to an enzyme that retains its biological activity at elevated temperatures (e.g., at 55° C. or higher), or retains its biological activity following repeated cycles of heating and cooling.

As used herein, an "amplifying polymerase activity" refers to an enzymatic activity that catalyzes the polymerization of deoxyribonucleotides or ribonucleotides. Generally, the enzyme will initiate synthesis at the 3'-end of the primer annealed to a target nucleic acid template sequence, and will proceed toward the 5' end of the template strand.

Non-limiting examples of thermostable DNA polymerases may include, but are not limited to, polymerases isolated from the thermophilic bacteria *Thermus aquaticus* (Taq polymerase), *Thermus thermophilus* (Tth polymerase), *Thermococcus litoralis* (Tli or VENT™ polymerase), *Pyrococcus furiosus* (Pfu or DEEPVENT™ polymerase), *Pyrococcus woosii* (Pwo polymerase) and other *Pyrococcus* species, *Bacillus stearothermophilus* (Bst polymerase), *Sulfolobus acidocaldarius* (Sac polymerase), *Thermoplasma acidophilum* (Tac polymerase), *Thermus rubber* (Tru polymerase), *Thermus brockianus* (DYNAZYME™ polymerase) i (Tne polymerase), *Thermotoga maritime* (Tma) and other species of the *Thermotoga* genus (Tsp polymerase), and *Methanobacterium thermoautotrophicum* (Mth polymerase). The PCR reaction may contain more than one thermostable polymerase enzyme with complementary properties leading to more efficient amplification of target sequences. For example, a nucleotide polymerase with high processivity (the ability to copy large nucleotide segments) may be complemented with another nucleotide polymerase with proofreading capabilities (the ability to correct mistakes during elongation of target nucleic acid sequence), thus creating a PCR reaction that can copy a long target sequence with high fidelity. The thermostable polymerase may be used in its wild type form. Alternatively, the polymerase may be modified to contain a fragment of the enzyme or to contain a mutation that provides beneficial properties to facilitate the PCR reaction.

In one embodiment, the thermostable polymerase may be Taq DNA polymerase. Many variants of Taq polymerase with enhanced properties are known and include, but are not limited to, AmpliTaq™, AmpliTaq™, Stoffel fragment, SuperTaq™, SuperTae™ plus, LA Taq™, LApro Taq™, and EX Taq™. In another embodiment, the thermostable polymerase is the AmpliTaq Stoffel fragment.

The "Substantially Double-Stranded Oligonucleotide"

The "substantially double-stranded oligonucleotide" refers to an oligonucleotide having at least one region that has a strand with one or more nucleotides engaged in complementary hydrogen bond pairs with one or more nucleotides of a region of another strand. Base-pairing in the substantially double-stranded region may comprise one or more contiguously base paired nucleotides or contiguously base paired nucleotides interspersed with one or more nucleotides that are not base-paired. A substantially double-stranded region may comprise one or more ribonucleotides or deoxyribonucleotides. The based-paired nucleotides may be situated at the 5' end or 3' end of one of the strands of the "substantially double-stranded oligonucleotide" or anywhere in between. The base-pairing in the substantially double-stranded region may be intermolecular or intermolecular. That is, the base pairing may be between two or more separate oligonucleotides (e.g., double-stranded oligonucleotides), or within a single oligonucleotide to form a stem and loop structure (e.g., hairpin oligonucleotides). In one embodiments the "substantially double-stranded oligonucleotide" may comprise 1, 2, 3, 4, 5 or more stem structures. The "substantially double-stranded oligonucleotide" may comprise about 1, about 2, about 3, about 4, about 5, about 6, about 7, about 8, about 9, about 10, about 15, about 20, about 25, about 50 or more base paired nucleotides. The "substantially double-stranded oligonucleotide" may comprise about 1, about 2, about 3, about 4, about 5, about 6, about 7, about 8, about 9, about 10, about 15, about 20, about 25, about 50 or more nucleotides that are not base paired.

In some embodiments, the "substantially double-stranded oligonucleotide" comprises two based paired oligonucleotides that are 100% complimentary to each other. In other embodiments, the "substantially double-stranded oligonucleotide" comprises two based paired oligonucleotides may have about 95%, about 90%, about 75%, about 50%, or less complementarity to each other.

The 5' end or 3' end of one of the strands in the "substantially double-stranded oligonucleotide" may have a 5' or 3' overhang at one or both ends of the oligonucleotide or one or both ends of the oligonucleotide may be base-paired and blunt-ended.

The amount of double-stranded oligonucleotide present can be estimated by knowing the oligonucleotide's melting temperature or Tm, i.e. the temperature at which about 50% of the oligonucleotide and its complement are in duplex.

The melting temperature (Tm) of a double stranded region of an oligonucleotide can be calculated from the oligonucleotide sequence using methods that are well known in the art.

For example, the Tm of an oligonucleotide can be calculated using the formulas (as described on Promega's web site):

$$T_m = 4° C. \times (\text{number of G's and C's in the primer}) + 2° C. \times (\text{number of A's and T's in the primer})$$

This formula is valid for oligonucleotides having a double stranded region of <14 bases and assumes that the reaction is carried out in the presence of 50 mM monovalent cations.

For longer oligonucleotides having a double stranded region>14 bases, the formula below can be used:

$T_m = 64.9°\,C. + 41°\,C. \times (\text{number of G's and C's in the primer} - 16.4)/N$ Where N is the length of the primer.

Another commonly used formula takes into account the salt concentration of the reaction (see Rychlik, W. and Rhoads, R. E. (1989) Nucl. Acids Res. 17, 8543; PCR Core Systems Technical Bulletin #TB254, Promega Corporation; Sambrook, J., Fritsch, E. F. and Maniatis, T. (1989) Molecular Cloning: A Laboratory Manual, Cold Spring Harbor Laboratory Press, Cold Spring Harbor, N.Y. and Mueller, P. R. et al. (1993) In: Current Protocols in Molecular Biology 15.5, Greene Publishing Associates, Inc. and John Wiley and Sons, New York).

This formula is as follows:

$T_m = 81.5°\,C. + 16.6°\,C. \times (\log_{10}[Na^+]+[K^+]) + 0.41°\,C. \times (\% GC) - 675/N$ Where N is the number of nucleotides in the oligonucleotide.

The most sophisticated $T_m$ calculations take into account the exact sequence and base stacking parameters, not just the base composition (as described in Borer P. N. et al. (1974) J. Mol. Biol. 86, 843; SantaLucia, J. (1998) Proc. Nat. Acad. Sci. USA 95, 1460; Allawi, H. T. and SantaLucia, J. Jr. (1997) Biochemistry 36, 10581 and von Ahsen N. et al. (1999) Clin. Chem. 45, 2094).

The equation used is:

$$T_m = \frac{\Delta H \frac{kcal}{°C. * Mol}}{\Delta S + R \ln([\text{primer}]/2)} - 2.73.15°\,C.$$

Where, ΔH is the enthalpy of base stacking interactions adjusted for helix initiation factors, ΔS is the entropy of base stacking adjusted for helix initiation factors and for the contributions of salts to the entropy of the system and R is the universal gas constant (1.987 Cal/° C. per Mol).

This equation, as implemented above, is valid if the following assumptions are met:

The primer is not self complementary. For self-complementary oligonucleotides, the denominator of the equation becomes ΔS+R ln([primer]/4)

The primer concentration is much greater than the target concentration. If the concentrations are almost equal, the denominator of the equation becomes ΔS+R ln([primer]−[target]/2)

The primer is an "oligonucleotide" rather than a long polymer. The salt effects on polymers is significantly different from those on oligos. For a complete discussion, see reference 6.

The melting temperature for different oligonucleotides can be conveniently determined using web-based calculators freely available on the web, e.g. the Biomath calculator on Promega's web site In one embodiment, the "substantially double-stranded oligonucleotide" has a Tm from about 50° C. to about 55° C. or about 60° C.

The appropriate Tm is selected to ensure the oligonucleotide is double-stranded at a temperature
(1) where it is desirable to inhibit the nucleic polymerase's catalytic activity, i.e. at temperatures from about 20° C. to about 50° C., and
(2) where the heat-activated hot start nuclease can cleave and disrupt the secondary structure of the substantially double-stranded oligonucleotide sufficiently to preclude the inhibition of the nucleic polymerase's catalytic activity.

In some embodiments, the "substantially double-stranded oligonucleotide" is chemically modified at its 3'-end and/or 5'-end. The modification of the oligonucleotide at its 3' end blocks the oligonucleotide from participating in primer extension.

In one embodiment, the oligonucleotide is blocked from participating in primer extension through the incorporation of a dideoxyribonucleotide at the 3' end.

For example, the 3'-terminus of a double stranded oligonucleotide may be capped at the 3' terminus with a dideoxythymine triphosphate using a Klenow fragment mutant (F762Y) of DNA polymerase I (Escherichia coli) or T7 DNA polymerase (Tabor, S, and Richardson, C. C., 1995, Proc. Natl. Acad. Sci. USA 92, 6339-6343). The 3'-OH terminus of the oligonucleotide is then extended with ddTTP by the polymerase at 20 µM ddTTP in the presence of 2 mM Mg2+ in 50 mM Tris pH 7.5 buffer, at 37° C. for 30 min. Following extension, the sample is placed in a 100° C. water bath for 3 min to denature the protein. Following heating the oligonucleotide sample was cooled slowly to ambient temperature (2-3 hrs) to allow formation of duplex structure.

In another embodiment, the substantially double-stranded oligonucleotide contains at least one RNA:DNA base pair that can be endonucleolytically cleaved by an RNase H activity. The location of the at least one RNA:DNA base pair is not particularly important provided any double stranded fragments produced by the cleavage of the double stranded oligonucleotide at the at least one RNA:DNA base pair have a Tm that is at least about 5-10° C. below the temperature of the PCR reaction's annealing step. Hence, any fragments of the double-stranded oligonucleotide produced by the cleavage are unable to interfere with the subsequent PCR reaction because, at temperatures above 55° C., the fragments remain single-stranded and are unable to either inhibit the nucleic acid polymerase or anneal to a DNA template and provide a substrate for primer extension.

In certain embodiments, the oligonucleotide may have one or more blocking agents. A blocking agent refers to a nucleotide (or derivatives thereof), modified oligonucleotides and/or one or more other modifications which are incorporated into the nucleic acid inhibitors of the invention to prevent or inhibit degradation or digestion of such nucleic acid molecules by DNase activity. One or multiple blocking agents may be incorporated in the nucleic acid inhibitors of the invention internally, at or near the 3' termini and/or at or near the 5' termini of the nucleic acid inhibitors. Preferably, such blocking agents are located, for linear inhibitor nucleic acid molecules, at or near the 3' termini and/or at or near the 5' termini and/or at the preferred cleavage position of the 5' to 3' exonuclease of such molecules (Lyamichev, V., Brow, M. A. D., and Dahlberg, J. E., (1993) Science, 260, 778-783). Preferably, such blocking agents prevent or inhibit degradation or digestion of the inhibitor nucleic acid molecules by exonuclease activity associated with the polymerase or reverse transcriptase used or that may be present in the synthesis reaction. For example, blocking agents for the invention prevent degradation or digestion of inhibitor nucleic acid molecules by 3' exonuclease activity and/or 5' exonuclease activity associated with a polymerase (e.g., a DNA polymerase). Preferred blocking agents in accordance with the invention include dideoxynucleotides and their derivatives such as ddATP, ddCTP, ddGTP, ddITP, and ddTTP. Other blocking agents for use in accordance with the invention include, but are not limited to, AZT, phosphoamide backbones (e.g., PNAs), 3'-dNTPs (e.g., Condycepin) or any nucleotide containing a blocking group, preferably at its 3'-position. Such blocking agents preferably act to inhibit or prevent exonuclease activity (e.g., 3'-exonuclease activity) from altering or digesting the inhibitory nucleic acids of the invention. In some embodiments, the 5'-terminal of the oligonucleotides of the present invention may be modified in order to make them resistant to 5'-to-3' exonuclease activity. One such modification may be to add an addition nucleotide to the 5'-end of the oligonucleotide in a 5'-5'-linkage (see, Koza. M. et al., Journal of Organic Chemistry 56:3757). This results in at the 5'-end of the oligonucleotide which results in the 5'-end having a 3' In another aspect, such blocking agents preferably inhibit or prevent polymerase activity of the polymerases from altering or changing (e.g., incorporating nucleotides) to the inhibitory nucleic acids of the invention.

In other embodiments, the oligonucleotide may have one or more hairpins. As used herein, the term "hairpin" is used to indicate the structure of an oligonucleotide in which one or more portions of the oligonucleotide form base pairs with one or more other portions of the oligonucleotide. When the two portions are base paired to form a double stranded portion of the oligonucleotide, the double stranded portion may be referred to as a stem. Thus, depending on the number of complementary portions used, a number of stems (preferably 1-10) may be formed. Additionally, formation of the one or more stems preferably allows formation of one or more loop structures in the hairpin molecule. In one aspect, any one or more of the loop structures may be cut or nicked at one or more sites within the loop or loops but preferably at least one loop is not so cut or nicked. The sequence of the oligonucleotide may be selected so as to vary the number of nucleotides which base pair to form the stem from about 3 nucleotides to about 100 or more nucleotides, from about 3 nucleotides to about 50 nucleotides, from about 3 nucleotides to about 25 nucleotides, and from about 3 to about 10 nucleotides. In addition, the sequence of the oligonucleotide may be varied so as to vary the number of nucleotides which do not form base pairs from 0 nucleotides to about 100 or more nucleotides, from 0 nucleotides to about 50 nucleotides, from 0 nucleotides to about 25 nucleotides or from 0 to about 10 nucleotides. The two portions of the oligonucleotide which base pair may be located anywhere or at any number of locations in the sequence of the oligonucleotide. In some embodiments, one base-pairing-portion of the oligonucleotide may include the 3'-terminal of the oligonucleotide. In some embodiments, one base-pairing-portion may include the 5'-terminal of the oligonucleotide. In some embodiments, one base-pairing-portion of the oligonucleotide may include the 3'-terminal while the other base-pairing-portion may include the 5'-terminal and, when base paired, the stem of the oligonucleotide is blunt ended. In other embodiments, the location of the base pairing portions of the oligonucleotide may be selected so as to form a 3'-overhang, a 5'-overhang and/or may be selected so that neither the 3'-nor the 5'-most nucleotides are involved in base pairing.

Hot Start Nuclease

As used herein, a "hot start" enzyme composition refers to compositions having an enzymatic activity that is inhibited at non-permissive temperatures, i.e. from about 25° C. to about 45° C. and activated or 'heat inducible' at temperatures compatible with a PCR reaction, e.g. from about 55° C. to about 95° C.

A "hot start" nuclease composition, as used herein, refers to a composition comprising an 'inducible' RNA or DNA endonuclease, e.g. heat-inducible, that when activated, can cleave specifically the double-stranded oligonucleotide.

In a preferred embodiment, the "hot start" nuclease is a 'hot start' RNase H that can cleave a double-stranded oligonucleotide comprising at least one RNA:DNA base pair.

In some embodiments, the Tm of an oligonucleotide is determined using the SYBR Green intercalating dye. At low temperature the oligonucleotide inhibitors described herein fold upon themselves to form a double stranded hairpin structure. SYBR Green when intercalated into this double stranded structure absorbs light at 497 nM and emits at 520 nM. 520 nM light emission is monitored as the sample is slowly heated. Near the melting point (Tm) the oligonucleotide slowly unfolds releasing free SYBR Green causing a net loss in total fluorescence. The Tm is the point at which 50% of the oligonucleotide is in its melted state.

RNase H hydrolyzes RNA in RNA-DNA hybrids. First identified in calf thymus, RNase H has subsequently been described in a variety of organisms. RNase H activity appears to be ubiquitous in eukaryotes and bacteria. Although RNase Hs form a family of proteins of varying molecular weight and nucleolytic activity, substrate requirements appear to be similar for the various isotypes. For example, most RNase Hs studied to date function as endonucleases and require divalent cations (e.g. $Mg^{2+}$, $Mn^{2+}$) to produce cleavage products with 5' phosphate and 3' hydroxyl termini.

In prokaryotes, RNase H have been cloned and extensively characterized (see Crooke, et al., (1995) Biochem J, 312 (Pt 2), 599-608; Lima, et al., (1997) J Biol Chem, 272, 27513-27516; Lima, et al., (1997) Biochemistry, 36, 390-398; Lima, et al., (1997) J Biol Chem, 272, 18191-18199; Lima, et al., (2007) Mol Pharmacol, 71, 83-91; Lima, et al., (2007) Mol Pharmacol, 71, 73-82; Lima, et al., (2003) J Biol Chem, 278, 14906-14912; Lima, et al., (2003) J Biol Chem, 278, 49860-49867; Itaya, M., Proc. Natl. Acad. Sci. USA, 1990, 87, 8587-8591). For example, E. coli RNase HII is 213 amino acids in length whereas RNase HI is 155 amino acids long. E. coli RNase HII displays only 17% homology with E. coli RNase HI. An RNase H cloned from S. typhimurium differed from E. coli RNase HI in only 11 positions and was 155 amino acids in length (Itaya, M. and Kondo K., Nucleic Acids Res., 1991, 19, 4443-4449).

Proteins that display RNase H activity have also been cloned and purified from a number of viruses, other bacteria and yeast (Wintersberger, U. Pharmac. Ther., 1990, 48, 259-280). In many cases, proteins with RNase H activity appear to be fusion proteins in which RNase H is fused to the amino or carboxy end of another enzyme, often a DNA or RNA polymerase. The RNase H domain has been consistently found to be highly homologous to E. coli RNase HI, but because the other domains vary substantially, the molecular weights and other characteristics of the fusion proteins vary widely.

In higher eukaryotes two classes of RNase H have been defined based on differences in molecular weight, effects of divalent cations, sensitivity to sulfhydryl agents and immunological cross-reactivity (Busen et al., Eur. J. Biochem., 1977, 74, 203-208). RNase HI enzymes are reported to have molecular weights in the 68-90 kDa range, be activated by either $Mn^{2+}$ or $Mg^{2+}$ and be insensitive to sulfhydryl agents. In contrast, RNase HII enzymes have been reported to have molecular weights ranging from 31-45 kDa, to require $Mg^{2+}$ to be highly sensitive to sulfhydryl agents and to be inhibited by $Mn^{2+}$ (Busen, W., and Hausen, P., Eur. J. Biochem., 1975, 52, 179-190; Kane, C. M., Biochemistry, 1988, 27, 3187-3196; Busen, W., J. Biol. Chem., 1982, 257, 7106-7108).

An enzyme with RNase HII characteristics has also been purified to near homogeneity from human placenta (Frank et al., Nucleic Acids Res., 1994, 22, 5247-5254). This protein has a molecular weight of approximately 33 kDa and is active in a pH range of 6.5-10, with a pH optimum of 8.5-9. The enzyme requires $Mg^{2+}$ and is inhibited by $Mn^{2+}$ and n-ethyl maleimide. The products of cleavage reactions have 3' hydroxyl and 5' phosphate termini.

A detailed comparison of RNases from different species is reported in Ohtani N, Haruki M, Morikawa M, Kanaya S. J Biosci Bioeng. 1999; 88(1):12-9.

Examples of RNase H enzymes, which may be employed in the embodiments, also include, but are not limited to, thermostable RNase H enzymes isolated from thermophilic organisms such as *Pyrococcus furiosus*, *Pyrococcus horikoshi*, *Thermococcus litoralis* or *Thermus thermophilus*.

Other RNase H enzymes that may be employed in the embodiments are described in, for example, U.S. Pat. No. 7,422,888 to Uemori or the published U.S. Patent Application No. 2009/0325169 to Walder, the contents of which are incorporated herein by reference.

In one embodiment, an RNase H enzyme is a thermostable RNase H with about 40%, 50%, 60%, 70%, 80%, 90%, 95% or 99% homology with the amino acid sequence of Pfu RNase HII (SEQ ID NO: 10), shown below.

```
                                        (SEQ ID NO: 10)
MKIGGIDEAG RGPAIGPLVV ATVVVDEKNI EKLRNIGVKD

SKQLTPHERK NLFSQITSIA 60

DDYKIVIVSP EEIDNRSGTM NELEVEKFAL ALNSLQIKPA

LIYADAADVD ANRFASLIER 120

RLNYKAKIIA EHKADAKYPV VSAASILAKV VRDEEIEKLK

KQYGDFGSGY PSDPKTKKWL 180

EEYYKKHNSF PPIVRRTWET VRKIEESIKA KKSQLTLDKF FKKP
```

The homology can be determined using, for example, a computer program DNASIS-Mac (Takara Shuzo), a computer algorithm FASTA (version 3.0; Pearson, W. R. et al., Pro. Natl. Acad. Sci., 85:2444-2448, 1988) or a computer algorithm BLAST (version 2.0, Altschul et al., Nucleic Acids Res. 25:3389-3402, 1997)

Figure 5:
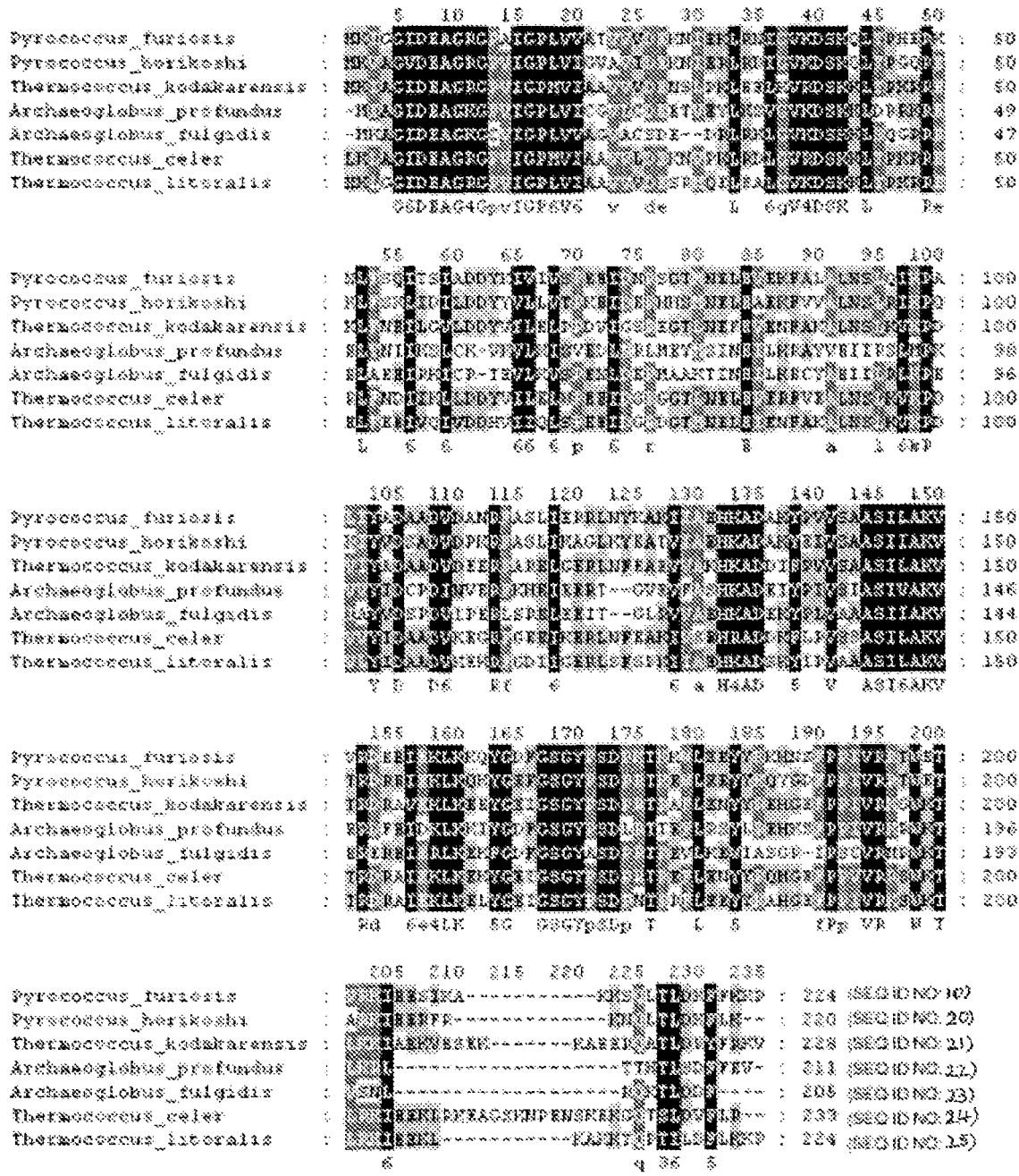
FIG. 5 depicts a sequence alignment between *Pyrococcus furiosis* (SEQ ID NO: 10), *Pyrococcus horikoshi* (SEQ ID NO: 20), *Thermococcus kodakarensis* (SEQ ID NO: 21), *Archeoglobus profundus* (SEQ ID NO: 22), *Archeoglobus fulgidis* (SEQ ID NO: 23), *Thermococcus celer* (SEQ ID NO: 24) and *Thermococcus litoralis* (SEQ ID NO: 25) RNase HII polypeptide sequences.

In another embodiment, an RNase H enzyme is a thermostable RNase H with at least one or more homology regions 1-4 corresponding to positions 5-20, 33-44, 132-150, and 158-173 of SEQ ID NO: 10. These homology regions were defined by sequence alignment of *Pyrococcus furiosis*, *Pyrococcus horikoshi*, *Thermococcus kodakarensis*, *Archeoglobus profundus*, *Archeoglobus fulgidis*, *Thermococcus celer* and *Thermococcus litoralis* RNase HII polypeptide sequences (see FIG. 5).

```
        (SEQ ID NO: 11; corresponding to positions 5-20
                              of SEQ ID NO: 10)
HOMOLOGY REGION 1: GIDEAG RGPAIGPLVV (SEQ ID NO: 12; corresponding to positions 33-44
                              of SEQ ID NO: 10)
HOMOLOGY REGION 2: LRNIGVKD SKQL (SEQ ID NO: 13; corresponding to positions 132-150
                              of SEQ ID NO: 10)
HOMOLOGY REGION 3: HKADAKYPV VSAASILAKV (SEQ ID NO: 14; corresponding to positions 158-173
                              of SEQ ID NO: 10)
HOMOLOGY REGION 4: KLK KQYGDFGSGY PSD
```

In one embodiment, an RNase H enzyme is a thermostable RNase H with at least one of the homology regions having about 50%, 60%. 70%, 80%, 90% sequence identity with a polypeptide sequence of SEQ ID NOs: 11, 12, 13 or 14.

In another embodiment, an RNase H enzyme is a thermostable RNase H with about 40%, 50%, 60%, 70%, 80%, 90%, 95% or 99% homology with the amino acid sequence of *Thermus thermophilus* RNase HI (SEQ ID NO: 15), shown below.

```
                                        (SEQ ID NO: 15)
MNPSPRKRVA LFTDGACLGN PGPGGWAALL RFHAHEKLLS

GGEACTTNNR MELKAAIEGL

KALKEPCEVD LYTDSHYLKK AFTEGWLEGW RKRGWRTAEG

KPVKNRDLWE ALLLAMAPHR

VRFHFVKGHT GHPENERVDR EARRQAQSQA KTPCPPRAPT

LFHEEA
```

In another embodiment, an RNase H enzyme is a thermostable RNase H with at least one or more homology regions 5-8 corresponding to positions 23-48, 62-69, 117-121 and 141-152 of SEQ ID NO: 15. These homology regions were defined by sequence alignment of *Haemophilus influenzae*, *Thermus thermophilis*, *Thermus acquaticus*, *Salmonella enterica* and *Agrobacterium tumefaciens* RNase HI polypeptide sequences (see FIG. 6).

```
         (SEQ ID NO: 16; corresponding to positions 23-48
                              of SEQ ID NO: 15)
HOMOLOGY REGION 5: K*V*LFTDG*C*GNPG*GG*ALLRY
``` where * denotes any amino acid.

```
         (SEQ ID NO: 17; corresponding to positions 62-69
                              of SEQ ID NO: 15)
HOMOLOGY REGION 6: TTNNRMEL (SEQ ID NO: 18; corresponding to positions 117-121
                              of SEQ ID NO: 15)
HOMOLOGY REGION 7: KPVKN (SEQ ID NO: 19; corresponding to positions 141-152
                              of SEQ ID NO: 15)
HOMOLOGY REGION 8: FVKGH*GH*ENE
```

In another embodiment, an RNase H enzyme is a thermostable RNase H with at least one of the homology regions 4-8 having about 50%, 60%. 70%, 80%, 90% sequence identity with a polypeptide sequence of SEQ ID NOs: 16, 17, 18 or 19.

The terms "sequence identity" as used herein refers to the extent that sequences are identical or functionally or structurally similar on a amino acid to amino acid basis over a window of comparison. Thus, a "percentage of sequence identity", for example, can be calculated by comparing two optimally aligned sequences over the window of comparison, determining the number of positions at which the identical amino acid occurs in both sequences to yield the number of matched positions, dividing the number of matched positions by the total number of positions in the window of comparison (i.e., the window size), and multiplying the result by 100 to yield the percentage of sequence identity.

Hot Start RNase H

In certain embodiments, the RNase H can be modified to produce a 'hot start' RNase H.

The term "modified RNase H," as used herein, can be an RNase H reversely coupled to or reversely bound to an inhibiting factor that causes the loss of the endonuclease activity of the RNase H. Release or decoupling of the inhibiting factor from the RNase H restores at least partial or full activity of the endonuclease activity of the RNase H. About 30-100% of its activity of an intact RNase H may be sufficient. The inhibiting factor may be a ligand or a chemical modification. The ligand can be an antibody, an aptamer, a receptor, a cofactor, or a chelating agent. The ligand can bind to the active site of the RNase H enzyme thereby inhibiting enzymatic activity or it can bind to a site remote from the RNase's active site. In some embodiments, the ligand may induce a conformational change. The chemical modification can be a crosslinking (for example, by formaldehyde) or acylation. The release or decoupling of the inhibiting factor from the RNase H may be accomplished by heating a sample or a mixture containing the coupled RNase H (inactive) to a temperature of about 65° C. to about 95° C. or higher, and/or lowering the pH of the mixture or sample to about 7.0 or lower.

As used herein, a 'hot start' RNase H activity refers to the herein described modified RNase H that has an endonuclease catalytic activity that can be regulated by association with a ligand. Under permissive conditions, the RNase H endonuclease catalytic activity is activated whereas at non-permissive conditions, this catalytic activity is inhibited. In some embodiments, the catalytic activity of a modified RNase H can be inhibited at temperature conducive for reverse transcription, i.e. about 42° C., and activated at more elevated temperatures found in PCR reactions, i.e. about 65° C. to 95° C. A modified RNase H with these characteristics is the to be "heat inducible."

In other embodiments, the catalytic activity of a modified RNase H can be regulated by changing the pH of a solution containing the enzyme.

Modifications of RNase H

Crosslinking of RNase H enzymes can be performed using, for example, formaldehyde. In one embodiment, a thermostable RNase H is subjected to controlled and limited crosslinking using formaldehyde. By heating an amplification reaction composition, which comprises the modified RNase H in an active state, to a temperature of about 95° C. or higher for an extended time, for example about 15 minutes, the crosslinking is reversed and the RNase H activity is restored.

In general, the lower the degree of crosslinking, the higher the endonuclease activity of the enzyme is after reversal of crosslinking. The degree of crosslinking may be controlled by varying the concentration of formaldehyde and the duration of crosslinking reaction. For example, about 0.2% (w/v), about 0.4% (w/v), about 0.6% (w/v), or about 0.8% (w/v) of formaldehyde may be used to crosslink an RNase H enzyme. About 10 minutes of crosslinking reaction using 0.6% formaldehyde may be sufficient to inactivate RNase HII from *Pyrococcus furiosus*.

The crosslinked RNase H does not show any measurable endonuclease activity at about 37° C. In some cases, a measurable partial reactivation of the crosslinked RNase H may occur at a temperature of around 50° C., which is lower than the PCR denaturation temperature. To avoid such unintended reactivation of the enzyme, it may be required to store or keep the modified RNase H at a temperature lower than 50° C. until its reactivation.

In general, PCR requires heating the amplification composition at each cycle to about 95° C. to denature the double stranded target sequence which will also release the inactivating factor from the RNase H, partially or fully restoring the activity of the enzyme.

RNase H may also be modified by subjecting the enzyme to acylation of lysine residues using an acylating agent, for example, a dicarboxylic acid. Acylation of RNase H may be performed by adding cis-aconitic anhydride to a solution of RNase H in an acylation buffer and incubating the resulting mixture at about 1-20° C. for 5-30 hours. In one embodiment, the acylation may be conducted at around 3-8° C. for 18-24 hours. The type of the acylation buffer is not particularly limited. In an embodiment, the acylation buffer has a pH of between about 7.5 to about 9.0.

The activity of acylated RNase H can be restored by lowering the pH of the amplification composition to about 7.0 or less. For example, when Tris buffer is used as a buffering agent, the composition may be heated to about 95° C., resulting in the lowering of pH from about 8.7 (at 25° C.) to about 6.5 (at 95° C.).

The duration of the heating step in the amplification reaction composition may vary depending on the modified RNase H, the buffer used in the PCR, and the like. However, in general, heating the amplification composition to 95° C. for about 30 seconds-4 minutes is sufficient to restore RNase H activity. In one embodiment, using a commercially available buffer and one or more non-ionic detergents, full activity of *Pyrococcus furiosus* RNase HII is restored after about 2 minutes of heating.

RNase H activity may be determined using methods that are well in the art. For example, according to a first method, the unit activity is defined in terms of the acid-solubilization of a certain number of moles of radiolabeled polyadenylic acid in the presence of equimolar polythymidylic acid under defined assay conditions (see Epicentre Hybridase thermostable RNase HI). In the second method, unit activity is defined in terms of a specific increase in the relative fluorescence intensity of a reaction containing equimolar amounts of the probe and a complementary template DNA under defined assay conditions.

Other 'Hot Start' Nucleases

In other embodiments, the hot start nuclease may be a heat-inducible thermostable sequence-specific endonuclease, such as a Type II Restriction Enzyme, that can cleave the 'substantially double-stranded oligonucleotide" but not sequences found within the targeted nucleic sequence to be amplified.

A number of thermostable restriction enzymes have been isolated from extremophile microorganisms. For example, the thermostable restriction endonuclease, PspGI, was purified from *Pyrococcus* sp. strain GI-H. PspGI is an isoschizomer of EcoRII and cleaves DNA before the first C in the sequence 5' CCWGG 3' (W is A or T). PspGI digestion can be carried out at 65 to 85° C. Recombinant PspGI has a half-life of 2 h at 95° C.

In certain embodiments, a thermostable restriction enzyme can be rendered 'heat inducible' by reversely coupling it to or reversely binding it to an inhibiting factor that causes the loss of the enzyme's catalytic activity at non-permissive temperatures. The inhibiting factor may be a ligand or a chemical modification. The ligand can be an antibody, an aptamer, a receptor, a cofactor, or a chelating agent. The ligand can bind to the active site of the thermostable restriction enzyme thereby inhibiting enzymatic activity or it can inhibit the catalytic activity by binding to a site remote from the thermostable restriction enzyme's active site. In some embodiments, the ligand may induce a conformational change. In another embodiment, the restriction enzyme may be modified by crosslinking (for example, by formaldehyde) or acylation. The release or decoupling of the inhibiting factor from the thermostable restriction enzyme may be accomplished by heating a sample or a mixture containing the coupled thermostable restriction enzyme (inactive) to a temperature of about 65° C. to about 95° C. or higher.

PCR Amplification of Target Nucleic Acid Sequences

Nucleic acid amplification can be accomplished by a variety of methods, including, but not limited to, the polymerase chain reaction (PCR), nucleic acid sequence based amplification (NASBA), ligase chain reaction (LCR), strand displacement amplification (SDA) reaction, transcription mediated amplification (TMA) reaction, and rolling circle amplification (RCA). The polymerase chain reaction (PCR) is the method most commonly used to amplify specific target DNA sequences.

"Polymerase chain reaction," or "PCR," generally refers to a method for amplification of a desired nucleotide sequence in vitro. Generally, the PCR process consists of introducing a molar excess of two or more extendable oligonucleotide primers to a reaction mixture comprising a sample having the desired target sequence(s), where the primers are complementary to opposite strands of the double stranded target sequence. The reaction mixture is subjected to a program of thermal cycling in the presence of a DNA polymerase, resulting in the amplification of the desired target sequence flanked by the DNA primers.

The technique of PCR is described in numerous publications, including, PCR: A Practical Approach, M. J. McPherson, et al., IRL Press (1991), PCR Protocols: A Guide to Methods and Applications, by Innis, et al., Academic Press (1990), and PCR Technology: Principals and Applications for DNA Amplification, H. A. Erlich, Stockton Press (1989). PCR is also described in many U.S. patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584, each of which is herein incorporated by reference.

The term "sample" refers to any substance containing nucleic acid material.

As used herein, the term "PCR fragment" or "reverse transcriptase-PCR fragment" or "amplicon" refers to a polynucleotide molecule (or collectively the plurality of molecules) produced following the amplification of a particular target nucleic acid. A PCR fragment is typically, but not exclusively, a DNA PCR fragment. A PCR fragment can be single-stranded or double-stranded, or in a mixture thereof in any concentration ratio. A PCR fragment or RT-PCT can be about 100 to about 500 nt or more in length.

A "buffer" is a compound added to an amplification reaction which modifies the stability, activity, and/or longevity of one or more components of the amplification reaction by regulating the pH of the amplification reaction. The buffering agents of the invention are compatible with PCR amplification and site-specific RNase H cleavage activity. Certain buffering agents are well known in the art and include, but are not limited to, Tris, Tricine, MOPS (3-(N-morpholino) propanesulfonic acid), and HEPES (4-(2-hydroxyethyl)-1-piperazineethanesulfonic acid). In addition, PCR buffers may generally contain up to about 70 mM KCl and about 1.5 mM or higher $MgCl_2$, to about 50-200 μM each of nucleotides dATP, dCTP, dGTP and dTTP. The buffers of the invention may contain additives to optimize efficient reverse transcriptase-PCR or PCR reaction.

An additive is a compound added to a composition which modifies the stability, activity, and/or longevity of one or more components of the composition. In certain embodiments, the composition is an amplification reaction composition. In certain embodiments, an additive inactivates contaminant enzymes, stabilizes protein folding, and/or decreases aggregation. Exemplary additives that may be included in an amplification reaction include, but are not limited to, ☐ine, formamide, KCl, $CaCl_2$, MgOAc, $MgCl_2$, NaCl, $NH_4OAc$, NaI, $Na(CO_3)_2$, LiCl, MnOAc, NMP, trehalose, demethylsulfoxide ("DMSO"), glycerol, ethylene glycol, dithiothreitol ("DTT"), pyrophosphatase (including, but not limited to *Thermoplasma acidophilum* inorganic pyrophosphatase ("TAP")), bovine serum albumin ("BSA"), propylene glycol, glycinamide, CHES, Percoll™, aurintricarboxylic acid, Tween 20, Tween 21, Tween 40, Tween 60, Tween 85, Brij 30, NP-40, Triton X-100, CHAPS, CHAPSO, Mackernium, LDAO (N-dodecyl-N,N-dimethylamine-N-oxide), Zwittergent 3-10, Xwittergent 3-14, Xwittergent SB 3-16, Empigen, NDSB-20, T4G32, *E. Coli* SSB, RecA, nicking endonucleases, 7-deazaG, dUTP, UNG, anionic detergents, cationic detergents, non-ionic detergents, zwittergent, sterol, osmolytes, cations, and any other chemical, protein, or cofactor that may alter the efficiency of amplification. In certain embodiments, two or more additives are included in an amplification reaction. According to the invention, additives may be added to improve selectivity of primer annealing provided the additives do not interfere with the activity of RNase H.

Reverse Transcriptase-PCR Amplification of a RNA Target Nucleic Acid Sequence

One of the most widely used techniques to study gene expression exploits first-strand cDNA for mRNA sequence(s) as template for amplification by the PCR.

The term "reverse transcriptase activity" and "reverse transcription" refers to the enzymatic activity of a class of polymerases characterized as RNA-dependent DNA polymerases that can synthesize a DNA strand (i.e., complementary DNA, cDNA) utilizing an RNA strand as a template.

"Reverse transcriptase-PCR" of "RNA PCR" is a PCR reaction that uses RNA template and a reverse transcriptase, or an enzyme having reverse transcriptase activity, to first generate a single stranded DNA molecule prior to the multiple cycles of DNA-dependent DNA polymerase primer elongation. Multiplex PCR refers to PCR reactions that produce more than one amplified product in a single reaction, typically by the inclusion of more than two primers in a single reaction.

Exemplary reverse transcriptases include, but are not limited to, the Moloney murine leukemia virus (M-MLV) RT as described in U.S. Pat. No. 4,943,531, a mutant form of M-MLV-RT lacking RNase H activity as described in U.S. Pat. No. 5,405,776, bovine leukemia virus (BLV) RT, Rous sarcoma virus (RSV) RT, Avian Myeloblastosis Virus (AMV) RT and reverse transcriptases disclosed in U.S. Pat. No. 7,883,871.

The reverse transcriptase-PCR procedure, carried out as either an end-point or real-time assay, involves two separate molecular syntheses: (i) the synthesis of cDNA from an RNA template; and (ii) the replication of the newly synthesized cDNA through PCR amplification. To attempt to address the technical problems often associated with reverse transcriptase-PCR, a number of protocols have been developed taking into account the three basic steps of the procedure: (a) the denaturation of RNA and the hybridization of reverse primer; (b) the synthesis of cDNA; and (c) PCR amplification. In the so called "uncoupled" reverse transcriptase-PCR procedure (e.g., two step reverse transcriptase-PCR), reverse transcription is performed as an independent step using the optimal buffer condition for reverse transcriptase activity. Following cDNA synthesis, the reaction is diluted to decrease $MgCl_2$, and deoxyribonucleoside triphosphate (dNTP) concentrations to conditions optimal for Taq DNA Polymerase activity, and PCR is carried out according to standard conditions (see U.S. Pat. Nos. 4,683,195 and 4,683,202). By contrast, "coupled" RT PCR methods use a common buffer optimized for reverse transcriptase and Taq DNA Polymerase activities. In one version, the annealing of reverse primer is a separate step preceding the addition of enzymes, which are then added to the single reaction vessel. In another version, the reverse transcriptase activity is a component of the thermostable Tth DNA polymerase. Annealing and cDNA synthesis are performed in the presence of $Mn^{2+}$ then PCR is carried out in the presence of $Mg^{2+}$ after the removal of $Mn^{2+}$ by a chelating agent. Finally, the "continuous" method (e.g., one step reverse transcriptase-PCR) integrates the three reverse transcriptase-PCR steps into a single continuous reaction that avoids the opening of the reaction tube for component or enzyme addition. Continuous reverse transcriptase-PCR has been described as a single enzyme system using the reverse transcriptase activity of thermostable Taq DNA Polymerase and Tth polymerase and as a two enzyme system using AMV RT and Taq DNA Polymerase wherein the initial 65° C. RNA denaturation step may be omitted.

In certain embodiments, one or more primers may be labeled. As used herein, "label," "detectable label," or "marker," or "detectable marker," which are interchangeably used in the specification, refers to any chemical moiety attached to a nucleotide, nucleotide polymer, or nucleic acid binding factor, wherein the attachment may be covalent or non-covalent. Preferably, the label is detectable and renders the nucleotide or nucleotide polymer detectable to the practitioner of the invention. Detectable labels include luminescent molecules, chemiluminescent molecules, fluorochromes, fluorescent quenching agents, colored molecules, radioisotopes or scintillants. Detectable labels also include any useful linker molecule (such as biotin, avidin, streptavidin, HRP, protein A, protein G, antibodies or fragments thereof, Grb2, polyhistidine, $Ni^{2+}$, FLAG tags, myc tags), heavy metals, enzymes (examples include alkaline phosphatase, peroxidase and luciferase), electron donors/acceptors, acridinium esters, dyes and calorimetric substrates. It is also envisioned that a change in mass may be considered a detectable label, as is the case of surface plasmon resonance detection. The skilled artisan would readily recognize useful detectable labels that are not mentioned above, which may be employed in the operation of the present invention.

One step reverse transcriptase-PCR provides several advantages over uncoupled reverse transcriptase-PCR. One step reverse transcriptase-PCR requires less handling of the reaction mixture reagents and nucleic acid products than uncoupled reverse transcriptase-PCR (e.g., opening of the reaction tube for component or enzyme addition in between the two reaction steps), and is therefore less labor intensive, reducing the required number of person hours. One step reverse transcriptase-PCR also requires less sample, and reduces the risk of contamination. The sensitivity and specificity of one-step reverse transcriptase-PCR has proven well suited for studying expression levels of one to several genes in a given sample or the detection of pathogen RNA. Typically, this procedure has been limited to use of gene-specific primers to initiate cDNA synthesis.

The ability to measure the kinetics of a PCR reaction by on-line detection in combination with these reverse transcriptase-PCR techniques has enabled accurate and precise quantitation of RNA copy number with high sensitivity. This has become possible by detecting the reverse transcriptase-PCR product through fluorescence monitoring and measurement of PCR product during the amplification process by fluorescent dual-labeled hybridization probe technologies, such as the 5' fluorogenic nuclease assay ("TaqMan™") or endonuclease assay ("CataCleave™"), discussed below.

Real-Time PCR Using a CataCleave™ Probe

Post amplification amplicon detection is both laborious and time consuming. Real-time methods have been developed to monitor amplification during the PCR process. These methods typically employ fluorescently labeled probes that bind to the newly synthesized DNA or dyes whose fluorescence emission is increased when intercalated into double stranded DNA. Real time detection methodologies are applicable to PCR detection of target nucleic acid sequences in genomic DNA or genomic RNA.

The probes are generally designed so that donor emission is quenched in the absence of target by fluorescence resonance energy transfer (FRET) between two chromophores. The donor chromophore, in its excited state, may transfer energy to an acceptor chromophore when the pair is in close proximity. This transfer is always non-radiative and occurs through dipole-dipole coupling. Any process that sufficiently increases the distance between the chromophores will decrease FRET efficiency such that the donor chromophore emission can be detected radiatively. Common donor chromophores include FAM, TAMRA, VIC, JOE, Cy3, Cy5, and Texas Red.) Acceptor chromophores are chosen so that their excitation spectra overlap with the emission spectrum of the donor. An example of such a pair is FAM-TAMRA. There are also non fluorescent acceptors that will quench a wide range of donors. Other examples of appropriate donor-acceptor FRET pairs will be known to those skilled in the art.

Common examples of FRET probes that can be used for real-time detection of PCR include molecular beacons (e.g., U.S. Pat. No. 5,925,517), TaqMan™ probes (e.g., U.S. Pat. Nos. 5,210,015 and 5,487,972), and CataCleave™ probes (e.g., U.S. Pat. No. 5,763,181). The molecular beacon is a single stranded oligonucleotide designed so that in the unbound state the probe forms a secondary structure where the donor and acceptor chromophores are in close proximity and donor emission is reduced. At the proper reaction temperature the beacon unfolds and specifically binds to the amplicon. Once unfolded the distance between the donor and acceptor chromophores increases such that FRET is reversed and donor emission can be monitored using specialized instrumentation. TaqMan™ and CataCleave™ technologies differ from the molecular beacon in that the FRET probes employed are cleaved such that the donor and acceptor chromophores become sufficiently separated to reverse FRET.

TaqMan™ technology employs a single stranded oligonucleotide probe that is labeled at the 5' end with a donor chromophore and at the 3' end with an acceptor chromophore. The DNA polymerase used for amplification must contain a 5'→3' exonuclease activity. The TaqMan™ probe binds to one strand of the amplicon at the same time that the primer binds. As the DNA polymerase extends the primer the polymerase will eventually encounter the bound TaqMan™ probe. At this time the exonuclease activity of the polymerase will sequentially degrade the TaqMan™ probe starting at the 5' end. As the probe is digested the mononucleotides comprising the probe are released into the reaction buffer. The donor diffuses away from the acceptor and FRET is reversed. Emission from the donor is monitored to identify probe cleavage. Because of the way TaqMan™ works a specific amplicon can be detected only once for every cycle of PCR. Extension of the primer through the TaqMan™ target site generates a double stranded product that prevents further binding of TaqMan™ probes until the amplicon is denatured in the next PCR cycle.

U.S. Pat. No. 5,763,181, of which content is incorporated herein by reference, describes another real-time detection method (referred to as "CataCleave™"). CataCleave™ technology differs from TaqMan™ in that cleavage of the probe is accomplished by a second enzyme that does not have polymerase activity. The CataCleave™ probe has a sequence within the molecule which is a target of an endonuclease, such as, for example a restriction enzyme or RNAase. In one example, the CataCleave™ probe has a chimeric structure where the 5' and 3' ends of the probe are constructed of DNA and the cleavage site contains RNA. The DNA sequence portions of the probe are labeled with a FRET pair either at the ends or internally. The PCR reaction includes a thermostable RNase H enzyme that can specifically cleave the RNA sequence portion of a RNA-DNA duplex. After cleavage, the two halves of the probe dissociate from the target amplicon at the reaction temperature and diffuse into the reaction buffer. As the donor and acceptors separate FRET is reversed in the same way as the TaqMan™ probe and donor emission can be monitored. Cleavage and dissociation regenerates a site for further CataCleave™ binding. In this way it is possible for a single amplicon to serve as a target or multiple rounds of probe cleavage until the primer is extended through the CataCleave™ probe binding site.

Labeling of a CataCleave™ Probe

The term "probe" comprises a polynucleotide that comprises a specific portion designed to hybridize in a sequence-specific manner with a complementary region of a specific nucleic acid sequence, e.g., a target nucleic acid sequence. In one embodiment, the oligonucleotide probe is in the range of 15-60 nucleotides in length. More preferably, the oligonucleotide probe is in the range of 18-30 nucleotides in length. The precise sequence and length of an oligonucleotide probe of the invention depends in part on the nature of the target polynucleotide to which it binds. The binding location and length may be varied to achieve appropriate annealing and melting properties for a particular embodiment. Guidance for making such design choices can be found in many of the references describing TaqMan™ assays or CataCleave™, described in U.S. Pat. Nos. 5,763, 181, 6,787,304, and 7,112,422, of which contents are incorporated herein by reference.

In certain embodiments, the probe is "substantially complementary" to the target nucleic acid sequence.

As used herein, the term "substantially complementary" refers to two nucleic acid strands that are sufficiently complimentary in sequence to anneal and form a stable duplex. The complementarity does not need to be perfect; there may be any number of base pair mismatches, for example, between the two nucleic acids. However, if the number of mismatches is so great that no hybridization can occur under even the least stringent hybridization conditions, the sequence is not a substantially complementary sequence. When two sequences are referred to as "substantially complementary" herein, it means that the sequences are sufficiently complementary to each other to hybridize under the selected reaction conditions. The relationship of nucleic acid complementarity and stringency of hybridization sufficient to achieve specificity is well known in the art. Two substantially complementary strands can be, for example, perfectly complementary or can contain from 1 to many mismatches so long as the hybridization conditions are sufficient to allow, for example discrimination between a pairing sequence and a non-pairing sequence. Accordingly, "substantially complementary" sequences can refer to sequences with base-pair complementarity of 100, 95, 90, 80, 75, 70, 60, 50 percent or less, or any number in between, in a double-stranded region.

As used herein, a "selected region" refers to a polynucleotide sequence of a target DNA or cDNA that anneals with the RNA sequences of a probe. In one embodiment, a "selected region" of a target DNA or cDNA can be from 1, 2, 3, 4, 5, 6, 7, 8, 9, 10, 11, 12, 13, 14, 15, 16, 17, 18, 19, 20, 21, 22, 23, 24, 25 or more nucleotides in length.

As used herein, the site-specific RNase H cleavage refers to the cleavage of the RNA moiety of the Catacleave™ probe that is entirely complimentary to and hybridizes with a target DNA sequence to form an RNA:DNA heteroduplex.

As used herein, "label" or "detectable label" of the CataCleave™ probe refers to any label comprising a fluorochrome compound that is attached to the probe by covalent or non-covalent means.

As used herein, "fluorochrome" refers to a fluorescent compound that emits light upon excitation by light of a shorter wavelength than the light that is emitted. The term "fluorescent donor" or "fluorescence donor" refers to a fluorochrome that emits light that is measured in the assays described in the present invention. More specifically, a fluorescent donor provides energy that is absorbed by a fluorescence acceptor. The term "fluorescent acceptor" or "fluorescence acceptor" refers to either a second fluorochrome or a quenching molecule that absorbs energy emitted from the fluorescence donor. The second fluorochrome absorbs the energy that is emitted from the fluorescence donor and emits light of longer wavelength than the light emitted by the fluorescence donor. The quenching molecule absorbs energy emitted by the fluorescence donor.

Any luminescent molecule, preferably a fluorochrome and/or fluorescent quencher may be used in the practice of this invention, including, for example, Alexa Fluor™ 350, Alexa Fluor™ 430, Alexa Fluor™ 488, Alexa Fluor™ 532, Alexa Fluor™ 546, Alexa Fluor™ 568, Alexa Fluor™ 594, Alexa Fluor™ 633, Alexa Fluor™ 647, Alexa Fluor™ 660, Alexa Fluor™ 680, 7-diethylaminocoumarin-3-carboxylic acid, Fluorescein, Oregon Green 488, Oregon Green 514, Tetramethylrhodamine, Rhodamine X, Texas Red dye, QSY 7, QSY33, Dabcyl, BODIPY FL, BODIPY 630/650, BODIPY 6501665, BODIPY TMR-X, BODIPY TR-X, Dialkylaminocoumarin, Cy5.5, Cy5, Cy3.5, Cy3, DTPA $(Eu^{3+})$-AMCA and $TTHA(Eu^{3+})$AMCA.

In one embodiment, the 3' terminal nucleotide of the oligonucleotide probe is blocked or rendered incapable of extension by a nucleic acid polymerase. Such blocking is conveniently carried out by the attachment of a reporter or quencher molecule to the terminal 3' position of the probe.

In one embodiment, reporter molecules are fluorescent organic dyes derivatized for attachment to the terminal 3' or terminal 5' ends of the probe via a linking moiety. Preferably, quencher molecules are also organic dyes, which may or may not be fluorescent, depending on the embodiment of the invention. For example, in a preferred embodiment of the invention, the quencher molecule is fluorescent. Generally whether the quencher molecule is fluorescent or simply releases the transferred energy from the reporter by non-radiative decay, the absorption band of the quencher should substantially overlap the fluorescent emission band of the reporter molecule. Non-fluorescent quencher molecules that absorb energy from excited reporter molecules, but which do not release the energy radiatively, are referred to in the application as chromogenic molecules.

Exemplary reporter-quencher pairs may be selected from xanthene dyes, including fluoresceins, and rhodamine dyes. Many suitable forms of these compounds are widely available commercially with substituents on their phenyl moieties which can be used as the site for bonding or as the bonding functionality for attachment to an oligonucleotide. Another group of fluorescent compounds are the naphthylamines, having an amino group in the alpha or □ position. Included among such naphthylamino compounds are 1-dimethylaminonaphthyl-5-sulfonate, 1-anilino-8-naphthalene sulfonate and 2-p-touidinyl6-naphthalene sulfonate. Other dyes include 3-phenyl-7-isocyanatocoumarin, acridines, such as 9-isothiocyanatoacridine and acridine orange, N-(p-(2-benzoxazolyl)phenyl)maleimide, benzoxadiazoles, stilbenes, pyrenes, and the like.

In one embodiment, reporter and quencher molecules are selected from fluorescein and rhodamine dyes.

There are many linking moieties and methodologies for attaching reporter or quencher molecules to the 5' or 3' termini of oligonucleotides, as exemplified by the following references: Eckstein, editor, Oligonucleotides and Analogues: A Practical Approach (IRL Press, Oxford, 1991); Zuckerman et al., Nucleic Acids Research, 15: 5305-5321 (1987) (3' thiol group on oligonucleotide); Sharma et al., Nucleic Acids Research, 19: 3019 (1991) (3' sulfhydryl); Giusti et al., PCR Methods and Applications, 2: 223-227 (1993) and Fung et al., U.S. Pat. No. 4,757,141 (5' phosphoamino group via Aminolink™ II available from Applied Biosystems, Foster City, Calif.) Stabinsky, U.S. Pat. No. 4,739,044 (3' aminoalkylphosphoryl group); Agrawal et al., Tetrahedron Letters, 31: 1543-1546 (1990) (attachment via phosphoramidate linkages); Sproat et al., Nucleic Acids Research, 15: 4837 (1987) (5' mercapto group); Nelson et al., Nucleic Acids Research, 17: 7187-7194 (1989) (3' amino group); and the like.

Rhodamine and fluorescein dyes are also conveniently attached to the 5' hydroxyl of an oligonucleotide at the conclusion of solid phase synthesis by way of dyes derivatized with a phosphoramidite moiety, e.g., Woo et al., U.S. Pat. No. 5,231,191; and Hobbs, Jr., U.S. Pat. No. 4,997,928.

Attachment of a CataCleave™ Probe to a Solid Support

In one embodiment, the oligonucleotide probe can be attached to a solid support. Different probes may be attached to the solid support and may be used to simultaneously detect different target sequences in a sample. Reporter molecules having different fluorescence wavelengths can be used on the different probes, thus enabling hybridization to the different probes to be separately detected.

Examples of preferred types of solid supports for immobilization of the oligonucleotide probe include controlled pore glass, glass plates, polystyrene, avidin coated polystyrene beads cellulose, nylon, acrylamide gel and activated dextran, controlled pore glass (CPG), glass plates and high cross-linked polystyrene. These solid supports are preferred for hybridization and diagnostic studies because of their chemical stability, ease of functionalization and well defined surface area. Solid supports such as controlled pore glass (500 Å, 1000 Å) and non-swelling high cross-linked polystyrene (1000 Å) are particularly preferred in view of their compatibility with oligonucleotide synthesis.

The oligonucleotide probe may be attached to the solid support in a variety of manners. For example, the probe may be attached to the solid support by attachment of the 3' or 5' terminal nucleotide of the probe to the solid support. However, the probe may be attached to the solid support by a linker which serves to distance the probe from the solid support. The linker is most preferably at least 30 atoms in length, more preferably at least 50 atoms in length.

Hybridization of a probe immobilized to a solid support generally requires that the probe be separated from the solid support by at least 30 atoms, more-preferably at least 50 atoms. In order to achieve this separation, the linker generally includes a spacer positioned between the linker and the 3' nucleoside. For oligonucleotide synthesis, the linker arm is usually attached to the 3'-OH of the 3' nucleoside by an ester linkage which can be cleaved with basic reagents to free the oligonucleotide from the solid support.

A wide variety of linkers are known in the art which may be used to attach the oligonucleotide probe to the solid support. The linker may be formed of any compound which does not significantly interfere with the hybridization of the target sequence to the probe attached to the solid support. The linker may be formed of a homopolymeric oligonucleotide which can be readily added on to the linker by automated synthesis. Alternatively, polymers such as functionalized polyethylene glycol can be used as the linker. Such polymers are preferred over homopolymeric oligonucleotides because they do not significantly interfere with the hybridization of probe to the target oligonucleotide. Polyethylene glycol is particularly preferred because it is commercially available, soluble in both organic and aqueous media, easy to functionalize, and completely stable under oligonucleotide synthesis and post-synthesis conditions.

The linkages between the solid support, the linker and the probe are preferably not cleaved during removal of base protecting groups under basic conditions at high temperature. Examples of preferred linkages include carbamate and amide linkages. Immobilization of a probe is well known in the art and one skilled in the art may determine the immobilization conditions.

According to one embodiment of the method, the CataCleave™ probe is immobilized on a solid support. The CataCleave™ probe comprises a detectable label and DNA and RNA nucleic acid sequences, wherein the probe's RNA nucleic acid sequences are entirely complementary to a selected region of the target DNA sequence and the probe's DNA nucleic acid sequences are substantially complementary to DNA sequences adjacent to the selected region of the target DNA sequence. The probe is then contacted with a sample of nucleic acids in the presence of RNase H and under conditions where the RNA sequences within the probe can form a RNA:DNA heteroduplex with the complementary DNA sequences in the PCR fragment. RNase H cleavage of the RNA sequences within the RNA:DNA heteroduplex results in a real-time increase in the emission of a signal from the label on the probe, wherein the increase in signal indicates the presence of the target DNA sequence.

According to another embodiment of the method, the CataCleave™ probe, immobilized on a solid support, comprises a detectable label and DNA and RNA nucleic acid sequences, wherein the probe's RNA nucleic acid sequences are entirely complementary to a selected region of the target DNA sequence and the probe's DNA nucleic acid sequences are substantially complementary to DNA sequences adjacent to the selected region of the target DNA sequence. The probe is then contacted with a sample of nucleic acids in the presence of RNase H and under conditions where the RNA sequences within the probe can form a RNA:DNA heteroduplex with the complementary DNA sequences in the PCR fragment. RNase H cleavage of the RNA sequences within the RNA:DNA heteroduplex results in a real-time increase in the emission of a signal from the label on the probe.

Immobilization of the probe to the solid support enables the target sequence hybridized to the probe to be readily isolated from the sample. In later steps, the isolated target sequence may be separated from the solid support and processed (e.g., purified, amplified) according to methods well known in the art depending on the particular needs of the researcher.

Kits

The disclosure herein also provides for a kit format which comprises a package unit having one or more reagents for the hot start amplification of a target nucleic acid. The kit may also contain one or more of the following items: buffers, instructions, and positive or negative controls. Kits may include containers of reagents mixed together in suitable proportions for performing the methods described herein. Reagent containers preferably contain reagents in unit quantities that obviate measuring steps when performing the subject methods.

Kits may also contain reagents for real-time PCR including, but not limited to, a hot start composition comprising a thermostable nucleic acid polymerase, hot start thermostable RNase H, a substantially double stranded oligonucleotide comprising at least one RNA:DNA base pair that is cleavable by RNase H, primers selected to amplify a target nucleic acid sequence and a labeled CataCleave™ oligonucleotide probe that anneals to the real-time PCR product and allows for the quantitative detection of the target nucleic acid sequence according to the methodology described herein.

In another embodiment, the kit reagents further comprised reagents for the extraction of genomic DNA or RNA from a biological sample. Kit reagents may also include reagents for reverse transcriptase-PCR analysis where applicable.

Any patent, patent application, publication, or other disclosure material identified in the specification is hereby incorporated by reference herein in its entirety. Any material, or portion thereof, that is the to be incorporated by reference herein, but which conflicts with existing definitions, statements, or other disclosure material set forth herein is only incorporated to the extent that no conflict arises between that incorporated material and the present disclosure material.

EXAMPLES

The following examples set forth methods for using the hot start composition according to the present invention. It is understood that the steps of the methods described in these examples are not intended to be limiting. Further objectives and advantages of the present invention other than those set forth above will become apparent from the examples which are not intended to limit the scope of the present invention.

Example 1

Polymerase Activity Using Cleavable and Non-Cleavable Oligonucleotide Inhibitors The ability of nucleic acid molecules to inhibit Taq DNA polymerase activity was examined in primer extension reactions. Taq DNA Polymerase was used to extend the M13 specific primer UPLong1 (SEQ ID NO: 1) using M13 single strand phage DNA as template. Two forms of an oligonucleotide inhibitor were used in this experiment. T-Pin 1 (SEQ ID NO: 2) was comprised of entirely DNA and is non-cleavable by active RNAse HII. T-Pin 4 (SEQ ID NO: 3) contained the identical base sequence as T-Pin 1 (SEQ ID NO: 2) with the substitution of two RNA bases that renders the T-Pin1 oligonucleotide cleavable by active RNAse HII. Test samples included Taq Polymerase (FIG. 1, A), Taq Polymerase+T-Pin 1 (SEQ ID NO: 2) (FIG. 1, B) and Taq Polymerase+T-Pin 4 (SEQ ID NO:3) (FIG. 1, C). Enzyme activities were tested in the absence of HotStart RNase HII (FIG. 1, black bars) and the presence of HotStart RNase HII (FIG. 1, gray bars). Each test condition consisted of 7 duplicate reactions used to monitor polymerase activity over time. The final concentration of each component in the 25 µl primer extension reactions was as follows:

1×PCR buffer, 24 nM UpLong 1 (SEQ ID NO: 1), 200 ng M13 ss DNA, 0.2 mM dATP, 0.2 mM dGTP, 0.2 mM dCTP, 0.4 mM dUTP.

Select reactions contained 5 U RNase HII. Taq DNA Polymerase was preincubated with or without 20 pmol oligonucleotide inhibitor/unit enzyme in 1×PCR buffer. The primer extension reactions were initiated by the addition of 0.25 U Taq. The reactions were incubated for 5 min at 95° C. followed by 30 min at 50° C. After the reactions reached 50° C., one of the replicates was sampled every 5 min for a total of 30 min by stopping the reaction with the addition of 2.5 µl of 250 mM EDTA. 50 µl of a 1:3000 dilution of Pico Green was added to each sample and the fluorescent output of each sample was monitored in the Roche LightCycler 480 for 10 cycles at 10 sec/cycle. Relative Taq activity was calculated as the slope of the regression curve generate for each sample set.

Referring to FIG. 1, reactions that contained either T-Pin 1 (SEQ ID NO: 2; B black bar) or T-Pin 4 (SEQ ID NO: 3; C black bar) displayed reduced activity of Taq polymerase after heating when no RNase HII was present due to the reversible nature of this inhibition.

However, when Hot Start RNase HII was added to the reactions, T-Pin 4 (SEQ ID NO: 3) was cleaved after the initial 95° C. heating step yielding active Taq Polymerase (C, gray bars). T-Pin 1 (SEQ ID NO: 2) continued to inhibit Taq polymerase even in the presence of RNase HII because the T-Pin 1 could not be cleaved by the activated RNase HII (B, gray bars).

Example 2

Cleavable Oligonucleotide Inhibitor Suppresses Primer Dimer Formation

Hot Start Taq polymerases are known to suppress primer dimer formation. This is due to the fact that the polymerase is inactive at low temperatures when the reaction is most susceptible to primer dimer formation. The ability of various forms of Taq DNA polymerase to resist primer dimer formation was tested by performing PCR reactions in the absence of a DNA template using primers known to form primer dimers. Taq and T-Pin 4 (SEQ ID NO: 3) were premixed at a ratio of 40 pmol inhibitor/U of enzyme. The final concentration of each component in the PCR reactions was as follows:

1×PCR buffer, 500 nM Bac-F3 (SEQ ID NO: 4), 500 nM Bac-R10 (SEQ ID NO: 5), 200 nM Bac-Probe3 (SEQ ID NO: 6), 80 µM dATP, 80 µM dGTP, 80 µM dCTP, 160 µM dUTP, 2.5 U Taq and 1:12500 dilution of SYBR Green. Select reactions contained 2.5 U RNase HII.

The PCR reactions were performed using the following cycling protocol:

| Temperature | Time | Cycles |
| --- | --- | --- |
| 95° C. | 5 min | 1 |
| 95° C. | 10 Sec | |
| 55° C. | 60 sec | 1 |
| 70° C. | 30 sec | |
| 95° C. | 10 Sec | |
| 55° C. | 10 sec | 50 |
| 70° C. | 30 sec | |

Each test condition was performed with 8 replicate samples. The average Cp representing the formation of primer dimer was compared for each test conditions. T-Pin 4 (SEQ ID NO: 3) (Table 1, C) delayed primer dimer formation by an average of 7 PCR cycles when compared to amplification with a non-HotStart Taq (Table 1, A). The delay of primer dimer formation using T-Pin 4 (SEQ ID NO:3) was comparable to that achieved with a commercially available antibody based HotStart Taq polymerase (Table 1, B and C).

TABLE 1

Cp of Primer Dimer

| A | B | C |
| --- | --- | --- |
| 30.24 | 34.97 | 37.64 |
| 30.36 | 34.55 | 44.05 |
| 30.54 | 35.79 | 39.05 |
| 30.39 | 34.97 | 35.77 |
| 30.5 | 40.62 | 37.06 |
| 30.48 | 35.5 | 36.77 |
| 30.4 | 36.52 | 36.09 |
| 29.64 | 35.54 | 36.52 |
| 30.32 | 36.06 | 37.87 |

Example 3

PCR Amplification Using Cleavable Oligonucleotide Inhibitor

Plasmid DNA containing a portion of the ripX gene sequence was amplified in a PCR reaction comparing various forms of HotStart Taq polymerse. Approximately 64 ng/µl of stock plasmid was initially diluted to 200 pg/µl. Additional 10 fold serial dilutions were performed from 64 pg/µl to 0.64 fg/µl. 2 µl of each plasmid dilution was used as PCR template. Taq and T-Pin 4 (SEQ ID NO: 3) were premixed at a ratio of 40 pmol inhibitor/U of enzyme. The final concentrations of each component in the PCR reactions were as follows 1×PCR buffer, 500 nM Bac-F3 (SEQ ID NO: 4), 500 nM Bac-R10 (SEQ ID NO: 5), 200 nM Bac-Probe3 (SEQ ID NO: 6), 80 µM dATP, 80 µM dGTP, 80 µM dCTP, 160 µl dUTP, 2.5 U Taq. Select reactions contained 2.5 U RNase HII.

The PCR reactions were performed using the following cycling protocol:

| Temperature | Time | Cycles |
| --- | --- | --- |
| 95° C. | 5 min | 1 |
| 95° C. | 10 Sec | |
| 55° C. | 60 sec | 1 |
| 70° C. | 30 sec | |
| 95° C. | 10 Sec | |
| 55° C. | 10 sec | 50 |
| 70° C. | 30 sec | |

Figure 2:
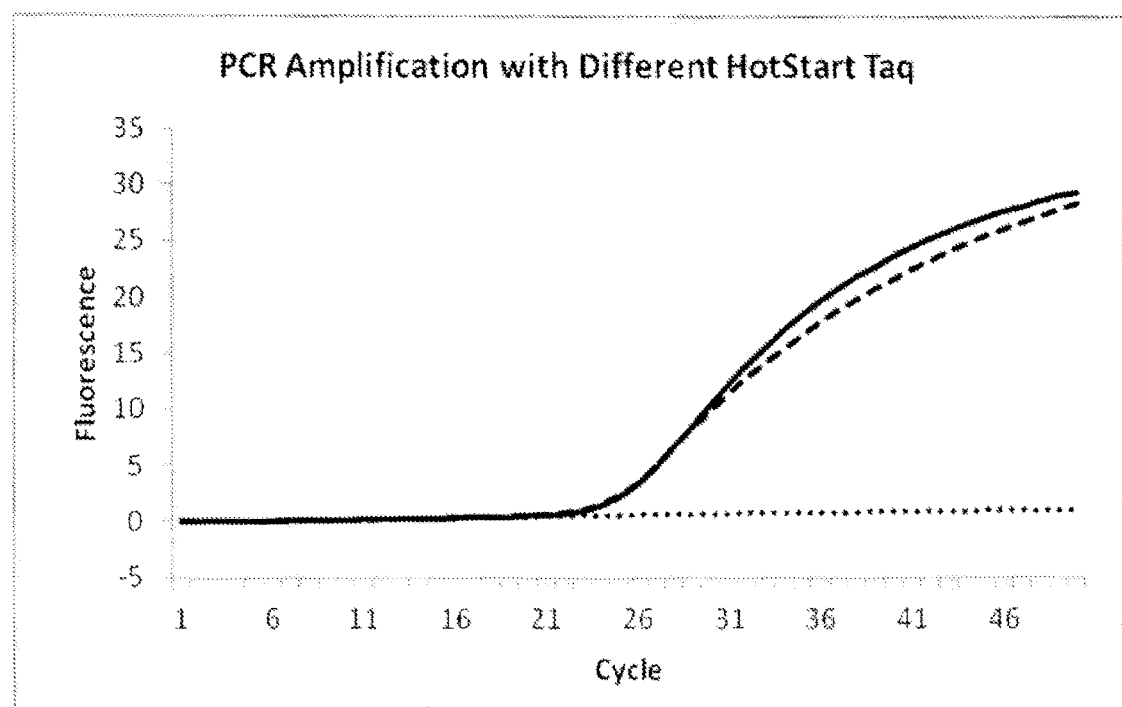
FIG. 2. depicts the amplification curve of an M13 DNA template in the presence of either (1) T-Pin 4 (SEQ ID NO: 3) but the absence of HotStart RNase HII (dotted line), (2) T-Pin 4 (SEQ ID NO: 3) but the presence of HotStart RNase HII (dashed line), or (3) a commercially available Platinum Taq which utilizes an antibody mediated HotStart (solid line).

FIG. 2 depicts the amplification curves generated when using 400 fg DNA template. The data demonstrates that T-Pin 4 (SEQ ID NO: 3) suppresses amplification when HotStart RNase HII is not supplied to the reaction (FIG. 2, dotted line). This is due to the fact that the inhibitory effect of T-Pin 4 (SEQ ID NO: 3) is reversible with respect to temperature cycling. When HotStart RNase HII is supplied to the reaction, T-Pin 4 (SEQ ID NO: 3) was cleaved by the enzyme after its activation and inhibition is relieved as demonstrated by the presence of the amplification curve (FIG. 2, dashed line). The commercially available Platinum Taq (FIG. 2, solid line), which utilizes an antibody mediated HotStart, yields a Cp value similar to the T-Pin 4 (SEQ ID NO: 3)+RNase HII.

Figure 3:
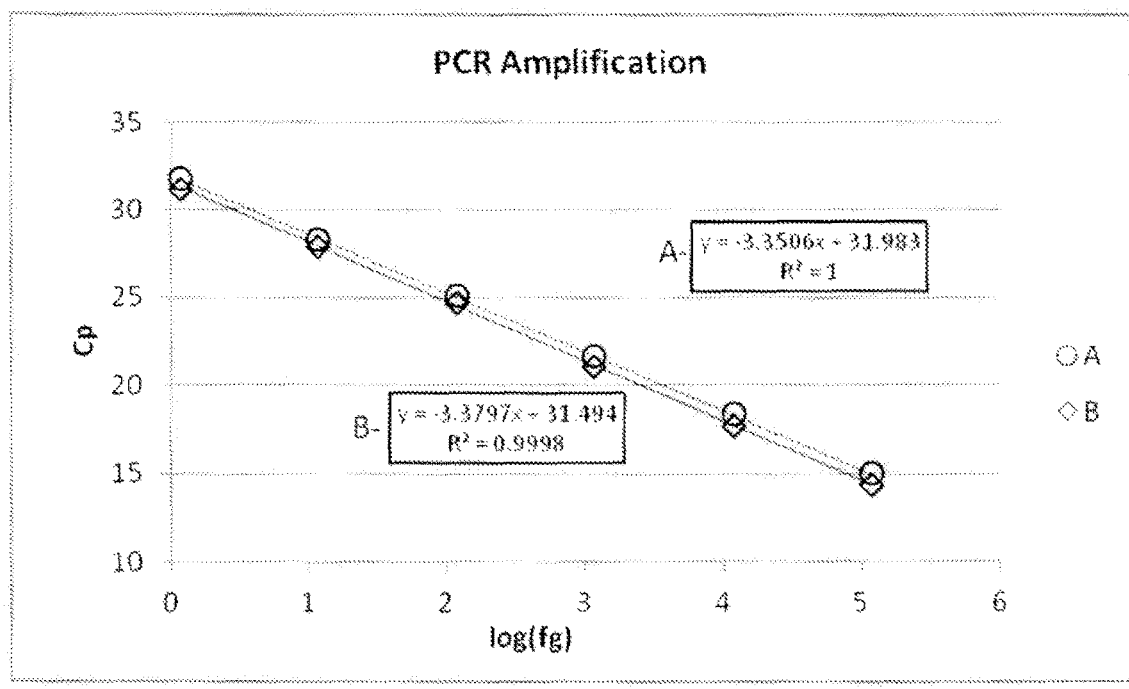
FIG. 3 depicts the calculated regression curve of Cp vs log [template concentration] for PCR reactions having Platinum Taq (FIG. 3, A) or Taq+T-Pin 4 (SEQ ID NO: 3)+HotStart RNase HII (FIG. 3, B).

FIG. 3 shows the calculated regression curve of Cp vs log (template concentration) for the dilution range of this PCR. The standard curves for this reaction are nearly identical for Platinum Taq (FIG. 3, A) and Taq+T-Pin 4 (SEQ ID NO: 3)+HotStart RNase HII (FIG. 3, B).

Example 4

RT-PCR Amplification Using Cleavable Oligonucleotide Inhibitor

HIV-1 genomic RNA was amplified in an RT-PCR reaction comparing various forms of HotStart Taq polymerase. Approximately 1.2 copies/µl of stock plasmid was initially diluted to 6×10⁵ copies/µl Additional 10 fold serial dilutions were performed from 6×10$^5$ copies/µl to 12 copies/V. 2 µl of each RNA dilution was used as PCR template. Taq and T-Pin 4 (SEQ ID NO: 3) were premixed at a ratio of 40 pmol inhibitor/U of enzyme.

The final concentrations of each component in the PCR reactions were as follows:

1×PCR buffer, 48 nM HIV-Pol-F3 (SEQ ID NO: 7), 48 nM HIV-Pol-R22 (SEQ ID NO: 8), 60 nM HIV-CCProbe24 (SEQ ID NO: 9), 100 µM dTTP, 200 µM dGTP, 200 µM dCTP, 200 µM dUTP, 200 µM dATP, 2.5 U Taq, 2 U Superscript III, 2.5 U RNase HII and 1 mM DTT.

The PCR reactions were performed using the following cycling protocol:

| Temperature | Time | Cycles |
| --- | --- | --- |
| 55° C. | 15 min | 1 |
| 95° C. | 5 min | 1 |
| 95° C. | 10 Sec | |
| 55° C. | 10 sec | 50 |
| 65° C. | 30 sec | |

Figure 4:
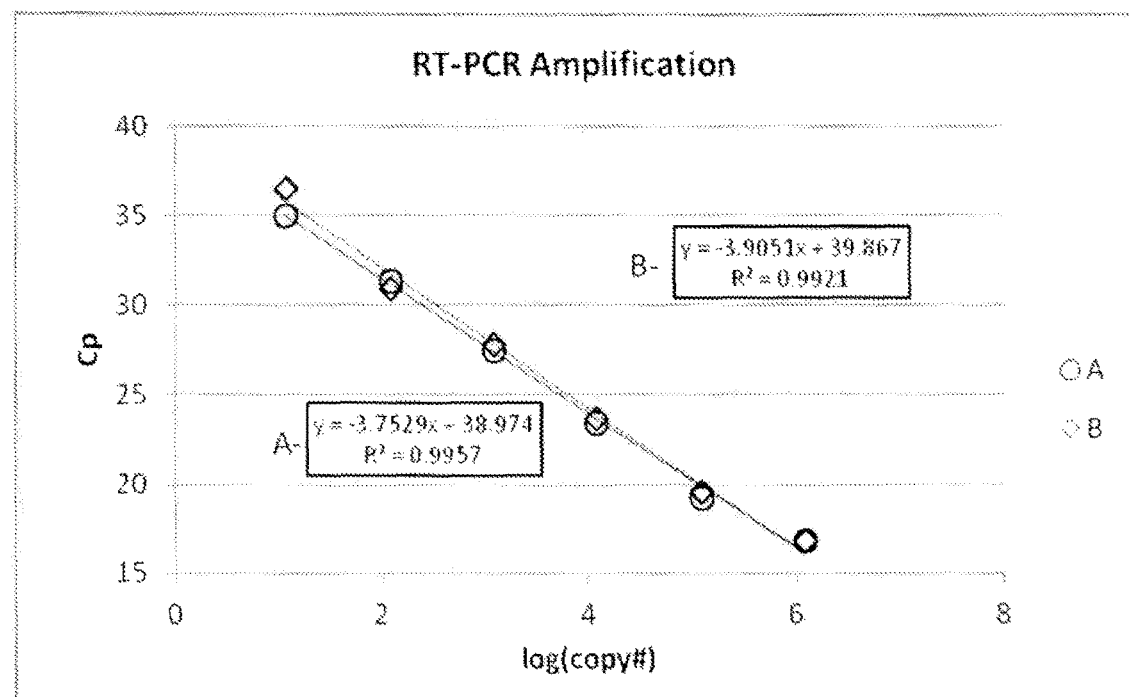
FIG. 4 depicts the calculated regression curve of Cp vs log [copy number] for RT-PCR reactions having Platinum Taq (FIG. 4, A) or Taq+T-Pin 4 (SEQ ID NO: 3)+HotStart RNase HII (FIG. 4, B).

FIG. 4 shows the calculated regression curve of Cp vs log (Copy number) for the dilution range of this PCR. The standard curves for this reaction are nearly identical for Platinum Taq (FIG. 4, A) and Taq+T-Pin4 (SEQ ID NO:3)+HotStart RNase HII (FIG. 4, B) demonstrating that this method performs well in RT-PCR reactions.

TABLE 2

PRIMER SEQUENCES

| SEQ ID NO: | Primer/ Probe | Sequence (5'-3') |
|---|---|---|
| 1 | UpLong1 | TTCCCAGTCACGACGTTGTAAAACGACGGCCAGTG |
| 2 | T-Pin1 | A*CATGTATTGATAGATCGACAAGATCTATCAATAC*/3SpC3 |
| 3 | T-Pin4 | A*CATGTATTGrATAGArUCGACAAGATCTATCAATAC*/3SpC3 |
| 4 | Bac-F3 | ATGCTTCGGCAAAGGAAG |
| 5 | Bac-R10 | CCTGAGTGTATGCGGAGT |
| 6 | Bac-Probe3 | 6-FAM/ATGCCGGCTTCCAATGCGAT/3IABlkFQ |
| 7 | HIV-Pol-F3 | GCAGTACAAATGGCAGTATTCATCCACAATT |
| 8 | HIV-Pol-R22 | CTCTGCTGTCCCTGTAATAAACCCGAAAATTT |
| 9 | HIV-CCProbe24 | 6-FAM/TTAAAAGAAAAGGGGrGrGrAUTGGGGGGTACA/3IABlkFQ | rA, rG, = RNA base, * = phosphorothioate bond

Any patent, patent application, publication, or other disclosure material identified in the specification is hereby incorporated by reference herein in its entirety. Any material, or portion thereof, that is said to be incorporated by reference herein, but which conflicts with existing definitions, statements, or other disclosure material set forth herein is only incorporated to the extent that no conflict arises between that incorporated material and the present disclosure material.

The invention claimed is:

1. A method of amplifying a target nucleic acid sequence, comprising:
   providing a sample to be tested for the presence of a target nucleic acid sequence;
   providing a pair of forward and reverse amplification primers, wherein the forward amplification primer anneals to the 5' end of the target nucleic acid sequence and the reverse amplification primer anneals to the 3' end of the target nucleic acid sequence;

providing a hot start enzyme composition comprising:
a Taq DNA polymerase,
an oligonucleotide of SEQ ID NO: 3, and
a hot start thermostable RNase HII; and
amplifying a polymerase chain reaction (PCR) fragment between the forward and reverse amplification primers in the presence of the target nucleic acid sequence, an amplification buffer and the hot start enzyme composition for at least one amplification cycle,
wherein the hot start thermostable RNase HII is activated by heat during a first amplification cycle of PCR and said oligonucleotide is cleaved by the activated hot start thermostable RNase HII during the first amplification cycle, thereby irreversibly abolishing the inhibition of said Taq DNA polymerase.

2. A method for the real-time detection of a target DNA sequence in a sample, comprising:
providing a sample to be tested for the presence of a target DNA sequence;
providing a pair of forward and reverse amplification primers, wherein the forward amplification primer anneals to the 5' end of the target nucleic acid sequence and the reverse amplification primer anneals to the 3' end of the target nucleic acid sequence;
providing a probe comprising a detectable label and DNA and RNA nucleic acid sequences, wherein the probe's RNA nucleic acid sequences are complementary to a selected region of the target DNA and the probe's DNA nucleic acid sequences are substantially complementary to sequences adjacent to the selected region of the target DNA sequence;
providing a hot start enzyme composition comprising:
a Taq DNA polymerase,
an oligonucleotide of SEQ ID NO: 3, and
a hot start thermostable RNase HII; and
amplifying a polymerase chain reaction (PCR) fragment between the forward and reverse amplification primers in the presence of the target DNA sequence, an amplification buffer, the hot start enzyme composition and the probe for at least one amplification cycle under conditions, wherein the hot start thermostable RNase HII is activated by heat during a first amplification cycle of PCR and said oligonucleotide is cleaved by the activated hot start thermostable RNase HII during the first amplification cycle thereby irreversibly abolishing the inhibition of said Taq DNA polymerase and the RNA sequences within the probe can form a RNA: DNA heteroduplex with complimentary sequences in the PCR fragment; and
detecting a real-time increase in the emission of a signal from the label on the probe, wherein the increase in signal indicates the presence of the target DNA sequence in the sample.

3. The method of claim 2, wherein the real-time increase in the emission of the signal from the label on the probe results from the RNase HII cleavage of the probe's RNA sequences in the RNA:DNA heteroduplex.

4. The method of claim 2, wherein the DNA and RNA sequences of the probe are covalently linked.

5. The method of claim 1, wherein the detectable label on the probe is a fluorescent label.

6. The method of claim 1, wherein the probe is labeled with a FRET pair.

7. The method of claim 1, wherein the PCR fragment or probe is linked to a solid support.

8. A method for the real-time detection of an RNA target sequence in a sample, comprising:
providing a sample to be tested for the presence of a target RNA sequence;
providing a pair of forward and reverse amplification primers, wherein the forward amplification primer anneals to the 5' end of a target nucleic acid sequence and the reverse amplification primer anneals to the 3' end of the target nucleic acid sequence;
providing a probe comprising a detectable label and DNA and RNA nucleic acid sequences, wherein the probe's RNA nucleic acid sequences are entirely complementary to a selected region of a target cDNA sequence and the probe's DNA nucleic acid sequences are substantially complementary to target DNA sequences adjacent to the selected region of the target cDNA sequence;
providing a hot start enzyme composition comprising:
a Taq DNA polymerase,
an oligonucleotide of SEQ ID NO: 3, and
a hot start thermostable RNase HII; and
reverse transcribing the target RNA in the presence of a reverse transcriptase and the reverse amplification primer to produce the target cDNA sequence;
amplifying a polymerase chain reaction (PCR) fragment between the forward and reverse amplification primers in the presence of the target cDNA sequence, the hot start enzyme composition, an amplification buffer and the probe for at least one amplification cycle under conditions, wherein the hot start thermostable RNase HII is activated by heat during a first amplification cycle of PCR and said oligonucleotide is cleaved by the activated hot start thermostable RNase HII during the first amplification cycle, thereby irreversibly abolishing the inhibition of said Taq DNA polymerase and the RNA sequences within the probe can form a RNA: DNA heteroduplex with complimentary sequences in the PCR fragment; and
detecting a real-time increase in the emission of a signal from the label on the probe, wherein the increase in signal indicates the presence of the target RNA sequences in the sample.

9. The method of claim 8, wherein the real-time increase in the emission of the signal from the label on the probe results from the RNase HII cleavage of the probe's RNA sequences in the RNA: DNA heteroduplex.

10. A method of amplifying a target nucleic acid sequence, comprising:
providing a sample to be tested for the presence of a target nucleic acid sequence;
providing a pair of forward and reverse amplification primers, wherein the forward amplification primer anneals to the 5' end of the target nucleic acid sequence and the reverse amplification primer anneals to the 3' end of the target nucleic acid sequence;
providing an enzyme composition comprising:
a Taq DNA polymerase, and
an oligonucleotide of SEQ ID NO: 3;
adding a hot start thermo stable RNase HII; and
amplifying a polymerase chain reaction (PCR) fragment between the forward and reverse amplification primers in the presence of the target nucleic acid sequence and an amplification buffer,
wherein the hot start thermostable RNase HII is activated by heat during a first amplification cycle of PCR and said oligonucleotide is cleaved by the activated hot start thermostable RNase HII, thereby irreversibly abolishing the inhibition of said Taq DNA polymerase.

11. A method for the real-time detection of a target DNA sequence in a sample, comprising:
providing a sample to be tested for the presence of a target DNA sequence;
providing a pair of forward and reverse amplification primers, wherein the forward amplification primer anneals to the 5' end of the target nucleic acid sequence and the reverse amplification primer anneals to the 3' end of the target nucleic acid sequence;
providing a probe comprising a detectable label and DNA and RNA nucleic acid sequences, wherein the probe's RNA nucleic acid sequences are entirely complementary to a selected region of the target DNA and the probe's DNA nucleic acid sequences are substantially complementary to sequences adjacent to the selected region of the target DNA sequence;
providing an enzyme composition comprising:
a Taq DNA polymerase, and
an oligonucleotide of SEQ ID NO: 3;
adding a hot start thermostable RNase HII;
amplifying a polymerase chain reaction (PCR) fragment between the forward and reverse amplification primers in the presence of the target DNA sequence, an amplification buffer, the enzyme composition and the probe for at least one amplification cycle under conditions, wherein the hot start thermostable RNase HII is activated by heat during a first amplification cycle of PCR and said oligonucleotide is cleaved by the activated hot start thermostable RNase HII thereby irreversibly abolishing the inhibition of said Taq DNA polymerase and the RNA sequences within the probe can form a RNA:DNA heteroduplex with complimentary sequences in the PCR fragment; and
detecting a real-time increase in the emission of a signal from the label on the probe, wherein the increase in signal indicates the presence of the target DNA sequence in the sample.

12. A method for the real-time detection of an RNA target sequence in a sample, comprising:
providing a sample to be tested for the presence of a target RNA sequence;
providing a pair of forward and reverse amplification primers, wherein the forward amplification primer anneals to the 5' end of a target nucleic acid sequence and the reverse amplification primer anneals to the 3' end of the target nucleic acid sequence;
providing a probe comprising a detectable label and DNA and RNA nucleic acid sequences, wherein the probe's RNA nucleic acid sequences are entirely complementary to a selected region of a target cDNA sequence and the probe's DNA nucleic acid sequences are substantially complementary to target DNA sequences adjacent to the selected region of the target cDNA sequence;
providing an enzyme composition comprising:
a Taq DNA polymerase, and
an oligonucleotide of SEQ ID NO: 3;
reverse transcribing the target RNA in the presence of a reverse transcriptase and the reverse amplification primer to produce the target cDNA sequence;
adding a hot start thermo stable RNase HII;
amplifying a polymerase chain reaction (PCR) fragment between the forward and reverse amplification primers in the presence of the target cDNA sequence, the enzyme composition, an amplification buffer and the probe for at least one amplification cycle under conditions, wherein the hot start thermostable RNase HII is activated by heat during a first amplification cycle of PCR and said oligonucleotide is cleaved by the activated hot start thermostable RNase HII, thereby irreversibly abolishing the inhibition of said Taq DNA polymerase and the RNA sequences within the probe can form a RNA:DNA heteroduplex with complimentary sequences in the PCR fragment; and
detecting a real-time increase in the emission of a signal from the label on the probe, wherein the increase in signal indicates the presence of the target RNA sequences in the sample.

13. The method according to claim 1 or 10, wherein the Taq DNA polymerase is a thermophilic nucleic polymerase.

14. The method according to claim 1 or 10, wherein the oligonucleotide is chemically modified at its 3'-end and/or 5'-end.

15. The method according to claim 1 or 10, wherein denaturation of the oligonucleotide produces at least two single-stranded oligonucleotides.

* * * * *

SEQUENCE LISTING

```
<160> NUMBER OF SEQ ID NOS: 29

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ttcccagtca cgacgttgta aaacgacggc cagtg                                35

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
acatgtattg atagatcgac aagatctatc aatac                                35

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
```
acatgtattg atagaucgac aagatctatc aatac         35

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atgcttcggc aaaggaag                            18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cctgagtgta tgcggagt                            18

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
atgccggctt ccaatgcgat                          20

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gcagtacaaa tggcagtatt catccacaat t              31

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ctctgctgtc cctgtaataa acccgaaaat tt             32

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
ttaaaagaaa aggggggaut gggggtaca                                           30

<210> SEQ ID NO 10
<211> LENGTH: 224
<212> TYPE: PRT
<213> ORGANISM: Pyrococcus furiosus

<400> SEQUENCE: 10

Met Lys Ile Gly Gly Ile Asp Glu Ala Gly Arg Gly Pro Ala Ile Gly
1               5                   10                  15

Pro Leu Val Val Ala Thr Val Val Asp Glu Lys Asn Ile Glu Lys
            20                  25                  30

Leu Arg Asn Ile Gly Val Lys Asp Ser Lys Gln Leu Thr Pro His Glu
        35                  40                  45

Arg Lys Asn Leu Phe Ser Gln Ile Thr Ser Ile Ala Asp Asp Tyr Lys
    50                  55                  60

Ile Val Ile Val Ser Pro Glu Glu Ile Asp Asn Arg Ser Gly Thr Met
65                  70                  75                  80

Asn Glu Leu Glu Val Glu Lys Phe Ala Leu Ala Leu Asn Ser Leu Gln
                85                  90                  95

Ile Lys Pro Ala Leu Ile Tyr Ala Asp Ala Ala Asp Val Asp Ala Asn
            100                 105                 110

Arg Phe Ala Ser Leu Ile Glu Arg Arg Leu Asn Tyr Lys Ala Lys Ile
        115                 120                 125

Ile Ala Glu His Lys Ala Asp Ala Lys Tyr Pro Val Val Ser Ala Ala
    130                 135                 140

Ser Ile Leu Ala Lys Val Val Arg Asp Glu Glu Ile Glu Lys Leu Lys
145                 150                 155                 160

Lys Gln Tyr Gly Asp Phe Gly Ser Gly Tyr Pro Ser Asp Pro Lys Thr
                165                 170                 175

Lys Lys Trp Leu Glu Glu Tyr Tyr Lys Lys His Asn Ser Phe Pro Pro
            180                 185                 190

Ile Val Arg Arg Thr Trp Glu Thr Val Arg Lys Ile Glu Glu Ser Ile
        195                 200                 205

Lys Ala Lys Lys Ser Gln Leu Thr Leu Asp Lys Phe Phe Lys Lys Pro
    210                 215                 220

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      consensus region peptide

<400> SEQUENCE: 11

Gly Ile Asp Glu Ala Gly Arg Gly Pro Ala Ile Gly Pro Leu Val Val
1               5                   10                  15

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      consensus region peptide

<400> SEQUENCE: 12

```
Leu Arg Asn Ile Gly Val Lys Asp Ser Lys Gln Leu
1               5                   10
```

```
<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic
      consensus region peptide

<400> SEQUENCE: 13

His Lys Ala Asp Ala Lys Tyr Pro Val Val Ser Ala Ala Ser Ile Leu
1               5                   10                  15

Ala Lys Val
```

```
<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      consensus region peptide

<400> SEQUENCE: 14

Lys Leu Lys Lys Gln Tyr Gly Asp Phe Gly Ser Gly Tyr Pro Ser Asp
1               5                   10                  15
```

```
<210> SEQ ID NO 15
<211> LENGTH: 166
<212> TYPE: PRT
<213> ORGANISM: Thermus thermophilus

<400> SEQUENCE: 15

Met Asn Pro Ser Pro Arg Lys Arg Val Ala Leu Phe Thr Asp Gly Ala
1               5                   10                  15

Cys Leu Gly Asn Pro Gly Pro Gly Gly Trp Ala Ala Leu Leu Arg Phe
            20                  25                  30

His Ala His Glu Lys Leu Leu Ser Gly Gly Glu Ala Cys Thr Thr Asn
        35                  40                  45

Asn Arg Met Glu Leu Lys Ala Ala Ile Glu Gly Leu Lys Ala Leu Lys
    50                  55                  60

Glu Pro Cys Glu Val Asp Leu Tyr Thr Asp Ser His Tyr Leu Lys Lys
65                  70                  75                  80

Ala Phe Thr Glu Gly Trp Leu Glu Gly Trp Arg Lys Arg Gly Trp Arg
                85                  90                  95

Thr Ala Glu Gly Lys Pro Val Lys Asn Arg Asp Leu Trp Glu Ala Leu
            100                 105                 110

Leu Leu Ala Met Ala Pro His Arg Val Arg Phe His Phe Val Lys Gly
        115                 120                 125

His Thr Gly His Pro Glu Asn Glu Arg Val Asp Arg Glu Ala Arg Arg
    130                 135                 140

Gln Ala Gln Ser Gln Ala Lys Thr Pro Cys Pro Pro Arg Ala Pro Thr
145                 150                 155                 160

Leu Phe His Glu Glu Ala
                165
```

```
<210> SEQ ID NO 16
<211> LENGTH: 25
<212> TYPE: PRT
```

-continued

```
<213> ORGANISM: Artificial Sequence
<220> FEATURE:
<223> OTHER INFORMATION: Description of Artificial Sequence: Synthetic
      consensus region peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (20)..(20)
<223> OTHER INFORMATION: Any amino acid

<400> SEQUENCE: 16

Lys Xaa Val Xaa Leu Phe Thr Asp Gly Xaa Cys Xaa Gly Asn Pro Gly
1               5                   10                  15

Xaa Gly Gly Xaa Ala Leu Leu Arg Tyr
            20                  25

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus region peptide

<400> SEQUENCE: 17

Thr Thr Asn Asn Arg Met Glu Leu
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus region peptide

<400> SEQUENCE: 18

Lys Pro Val Lys Asn
1               5

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      consensus region peptide
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
```

<222> LOCATION: (9)..(9)
<223> OTHER INFORMATION: Any amino acid

<400> SEQUENCE: 19

Phe Val Lys Gly His Xaa Gly His Xaa Glu Asn Glu
1               5                   10

<210> SEQ ID NO 20
<211> LENGTH: 220
<212> TYPE: PRT
<213> ORGANISM: Pyrococcus horikoshi

<400> SEQUENCE: 20

Met Lys Val Ala Gly Val Asp Glu Ala Gly Arg Gly Pro Val Ile Gly
1               5                   10                  15

Pro Leu Val Ile Gly Val Ala Val Ile Asp Glu Lys Asn Ile Glu Arg
                20                  25                  30

Leu Arg Asp Ile Gly Val Lys Asp Ser Lys Gln Leu Thr Pro Gly Gln
            35                  40                  45

Arg Glu Lys Leu Phe Ser Lys Leu Ile Asp Ile Leu Asp Asp Tyr Tyr
        50                  55                  60

Val Leu Leu Val Thr Pro Lys Glu Ile Asp Glu Arg His His Ser Met
65                  70                  75                  80

Asn Glu Leu Glu Ala Glu Lys Phe Val Val Ala Leu Asn Ser Leu Arg
                85                  90                  95

Ile Lys Pro Gln Lys Ile Tyr Val Asp Ser Ala Asp Val Asp Pro Lys
            100                 105                 110

Arg Phe Ala Ser Leu Ile Lys Ala Gly Leu Lys Tyr Glu Ala Thr Val
        115                 120                 125

Ile Ala Glu His Lys Ala Asp Ala Lys Tyr Glu Ile Val Ser Ala Ala
    130                 135                 140

Ser Ile Ile Ala Lys Val Thr Arg Asp Arg Glu Ile Glu Lys Leu Lys
145                 150                 155                 160

Gln Lys Tyr Gly Glu Phe Gly Ser Gly Tyr Pro Ser Asp Pro Arg Thr
                165                 170                 175

Lys Glu Trp Leu Glu Glu Tyr Tyr Lys Gln Tyr Gly Asp Phe Pro Pro
            180                 185                 190

Ile Val Arg Arg Thr Trp Glu Thr Ala Arg Lys Ile Glu Glu Arg Phe
        195                 200                 205

Arg Lys Asn Gln Leu Thr Leu Asp Lys Phe Leu Lys
    210                 215                 220

<210> SEQ ID NO 21
<211> LENGTH: 228
<212> TYPE: PRT
<213> ORGANISM: Thermococcus kodakarensis

<400> SEQUENCE: 21

Met Lys Ile Ala Gly Ile Asp Glu Ala Gly Arg Gly Pro Val Ile Gly
1               5                   10                  15

Pro Met Val Ile Ala Ala Val Val Asp Glu Asn Ser Leu Pro Lys
                20                  25                  30

Leu Glu Glu Leu Lys Val Arg Asp Ser Lys Lys Leu Thr Pro Lys Arg
            35                  40                  45

Arg Glu Lys Leu Phe Asn Glu Ile Leu Gly Val Leu Asp Asp Tyr Val
        50                  55                  60

Ile Leu Glu Leu Pro Pro Asp Val Ile Gly Ser Arg Glu Gly Thr Leu

```
            65                  70                  75                  80
Asn Glu Phe Glu Val Glu Asn Phe Ala Lys Ala Leu Asn Ser Leu Lys
                85                  90                  95

Val Lys Pro Asp Val Ile Tyr Ala Asp Ala Ala Asp Val Asp Glu Glu
            100                 105                 110

Arg Phe Ala Arg Glu Leu Gly Glu Arg Leu Asn Phe Glu Ala Glu Val
            115                 120                 125

Val Ala Lys His Lys Ala Asp Asp Ile Phe Pro Val Val Ser Ala Ala
            130                 135                 140

Ser Ile Leu Ala Lys Val Thr Arg Asp Arg Ala Val Glu Lys Leu Lys
145                 150                 155                 160

Glu Glu Tyr Gly Glu Ile Gly Ser Gly Tyr Pro Ser Asp Pro Arg Thr
                165                 170                 175

Arg Ala Phe Leu Glu Asn Tyr Tyr Arg Glu His Gly Glu Phe Pro Pro
            180                 185                 190

Ile Val Arg Lys Gly Trp Lys Thr Leu Lys Lys Ile Ala Glu Lys Val
            195                 200                 205

Glu Ser Glu Lys Lys Ala Glu Glu Arg Gln Ala Thr Leu Asp Arg Tyr
    210                 215                 220

Phe Arg Lys Val
225

<210> SEQ ID NO 22
<211> LENGTH: 211
<212> TYPE: PRT
<213> ORGANISM: Archeoglobus profundus

<400> SEQUENCE: 22

Met Ile Ala Gly Ile Asp Glu Ala Gly Lys Gly Pro Val Ile Gly Pro
1               5                   10                  15

Leu Val Ile Cys Gly Val Leu Cys Asp Glu Glu Thr Val Glu Tyr Leu
            20                  25                  30

Lys Ser Val Gly Val Lys Asp Ser Lys Leu Asp Arg Arg Lys Arg
            35                  40                  45

Glu Glu Leu Tyr Asn Ile Ile Lys Ser Leu Cys Lys Val Lys Val Leu
    50                  55                  60

Lys Ile Ser Val Glu Asp Leu Asn Arg Leu Met Glu Tyr Met Ser Ile
65                  70                  75                  80

Asn Glu Ile Leu Lys Arg Ala Tyr Val Glu Ile Arg Ser Leu Met
                85                  90                  95

Pro Lys Val Val Tyr Ile Asp Cys Pro Asp Ile Asn Val Glu Arg Phe
            100                 105                 110

Lys His Glu Ile Glu Glu Arg Thr Gly Val Glu Val Phe Ala Ser His
            115                 120                 125

Lys Ala Asp Glu Ile Tyr Pro Ile Val Ser Ile Ala Ser Ile Val Ala
            130                 135                 140

Lys Val Glu Arg Asp Phe Glu Ile Asp Lys Leu Lys Lys Ile Tyr Gly
145                 150                 155                 160

Asp Phe Gly Ser Gly Tyr Pro Ser Asp Leu Arg Thr Ile Glu Phe Leu
                165                 170                 175

Arg Ser Tyr Leu Arg Glu His Lys Ser Phe Pro Pro Ile Val Arg Lys
            180                 185                 190

Arg Trp Lys Thr Leu Lys Arg Leu Thr Thr His Thr Leu Ser Asp Phe
            195                 200                 205
```

```
Phe Glu Val
    210

<210> SEQ ID NO 23
<211> LENGTH: 205
<212> TYPE: PRT
<213> ORGANISM: Archeoglobus fulgidis

<400> SEQUENCE: 23

Met Lys Ala Gly Ile Asp Glu Ala Gly Lys Gly Cys Val Ile Gly Pro
1               5                   10                  15

Leu Val Val Ala Gly Val Ala Cys Ser Asp Glu Asp Arg Leu Arg Lys
            20                  25                  30

Leu Gly Val Lys Asp Ser Lys Lys Leu Ser Gln Gly Arg Arg Glu Glu
        35                  40                  45

Leu Ala Glu Glu Ile Arg Lys Ile Cys Arg Thr Glu Val Leu Lys Val
    50                  55                  60

Ser Pro Glu Asn Leu Asp Glu Arg Met Ala Ala Lys Thr Ile Asn Glu
65                  70                  75                  80

Ile Leu Lys Glu Cys Tyr Ala Glu Ile Ile Leu Arg Leu Lys Pro Glu
                85                  90                  95

Ile Ala Tyr Val Asp Ser Pro Asp Val Ile Pro Glu Arg Leu Ser Arg
            100                 105                 110

Glu Leu Glu Glu Ile Thr Gly Leu Arg Val Val Ala Glu His Lys Ala
        115                 120                 125

Asp Glu Lys Tyr Pro Leu Val Ala Ala Ser Ile Ile Ala Lys Val
    130                 135                 140

Glu Arg Glu Arg Glu Ile Glu Arg Leu Lys Glu Lys Phe Gly Asp Phe
145                 150                 155                 160

Gly Ser Gly Tyr Ala Ser Asp Pro Arg Thr Arg Glu Val Leu Lys Glu
                165                 170                 175

Trp Ile Ala Ser Gly Arg Ile Pro Ser Cys Val Arg Met Arg Trp Lys
            180                 185                 190

Thr Val Ser Asn Leu Arg Gln Lys Thr Leu Asp Asp Phe
        195                 200                 205

<210> SEQ ID NO 24
<211> LENGTH: 233
<212> TYPE: PRT
<213> ORGANISM: Thermococcus celer

<400> SEQUENCE: 24

Leu Lys Leu Ala Gly Ile Asp Glu Ala Gly Arg Gly Pro Val Ile Gly
1               5                   10                  15

Pro Met Val Ile Ala Ala Val Val Leu Asp Glu Lys Asn Val Pro Lys
            20                  25                  30

Leu Arg Asp Leu Gly Val Arg Asp Ser Lys Lys Leu Thr Pro Lys Arg
        35                  40                  45

Arg Glu Arg Leu Phe Asn Asp Ile Ile Lys Leu Leu Asp Asp Tyr Val
    50                  55                  60

Ile Leu Glu Leu Trp Pro Glu Glu Ile Asp Ser Arg Gly Gly Thr Leu
65                  70                  75                  80

Asn Glu Leu Glu Val Glu Arg Phe Val Glu Ala Leu Asn Ser Leu Lys
                85                  90                  95

Val Lys Pro Asp Val Val Tyr Ile Asp Ala Ala Asp Val Lys Glu Gly
            100                 105                 110
```

Arg Phe Gly Glu Glu Ile Lys Glu Arg Leu Asn Phe Glu Ala Lys Ile
            115                 120                 125

Val Ser Glu His Arg Ala Asp Asp Lys Phe Leu Pro Val Ser Ser Ala
    130                 135                 140

Ser Ile Leu Ala Lys Val Thr Arg Asp Arg Ala Ile Glu Lys Leu Lys
145                 150                 155                 160

Glu Lys Tyr Gly Glu Ile Gly Ser Gly Tyr Pro Ser Asp Pro Arg Thr
                165                 170                 175

Arg Glu Phe Leu Glu Asn Tyr Tyr Arg Gln His Gly Glu Phe Pro Pro
            180                 185                 190

Val Val Arg Arg Ser Trp Lys Thr Leu Arg Lys Ile Glu Glu Lys Leu
            195                 200                 205

Arg Lys Glu Ala Gly Ser Lys Asn Pro Glu Asn Ser Lys Glu Lys Gly
    210                 215                 220

Gln Ile Ser Leu Asp Val Phe Leu Arg
225                 230

<210> SEQ ID NO 25
<211> LENGTH: 224
<212> TYPE: PRT
<213> ORGANISM: Thermococcus litoralis

<400> SEQUENCE: 25

Met Lys Leu Gly Gly Ile Asp Glu Ala Gly Arg Gly Pro Val Ile Gly
1               5                   10                  15

Pro Leu Val Ile Ala Ala Val Val Asp Glu Ser Arg Met Gln Glu
            20                  25                  30

Leu Glu Ala Leu Gly Val Lys Asp Ser Lys Lys Leu Thr Pro Lys Arg
            35                  40                  45

Arg Glu Glu Leu Phe Glu Glu Ile Val Gln Ile Val Asp Asp His Val
    50                  55                  60

Ile Ile Gln Leu Ser Pro Glu Glu Ile Asp Gly Arg Asp Gly Thr Met
65                  70                  75                  80

Asn Glu Leu Glu Ile Glu Asn Phe Ala Lys Ala Leu Asn Ser Leu Lys
                85                  90                  95

Val Lys Pro Asp Val Leu Tyr Ile Asp Ala Ala Asp Val Lys Glu Lys
            100                 105                 110

Arg Phe Gly Asp Ile Ile Gly Glu Arg Leu Ser Phe Ser Pro Lys Ile
            115                 120                 125

Ile Ala Glu His Lys Ala Asp Ser Lys Tyr Ile Pro Val Ala Ala Ala
    130                 135                 140

Ser Ile Leu Ala Lys Val Thr Arg Asp Arg Ala Ile Glu Lys Leu Lys
145                 150                 155                 160

Glu Leu Tyr Gly Glu Ile Gly Ser Gly Tyr Pro Ser Asp Pro Asn Thr
                165                 170                 175

Arg Arg Phe Leu Glu Glu Tyr Tyr Lys Ala His Gly Glu Phe Pro Pro
            180                 185                 190

Ile Val Arg Lys Ser Trp Lys Thr Leu Arg Lys Ile Glu Glu Lys Leu
            195                 200                 205

Lys Ala Lys Lys Thr Gln Pro Thr Ile Leu Asp Phe Leu Lys Lys Pro
    210                 215                 220

<210> SEQ ID NO 26
<211> LENGTH: 174
<212> TYPE: PRT
<213> ORGANISM: Haemophilus influenzae

<400> SEQUENCE: 26

Met Phe Asn Leu Ser Leu Ser Ile Lys Ile Pro Ala Ile Leu His Asn
1               5                   10                  15

Asn Leu Phe Val Met Gln Lys Gln Ile Glu Ile Phe Thr Asp Gly Ser
                20                  25                  30

Cys Leu Gly Asn Pro Gly Ala Gly Gly Ile Gly Ala Val Leu Arg Tyr
            35                  40                  45

Lys Gln His Glu Lys Met Leu Ser Lys Gly Tyr Phe Lys Thr Thr Asn
        50                  55                  60

Asn Arg Met Glu Leu Arg Ala Val Ile Glu Ala Leu Asn Thr Leu Lys
65                  70                  75                  80

Glu Pro Cys Leu Ile Thr Leu Tyr Ser Asp Ser Gln Tyr Met Lys Asn
                85                  90                  95

Gly Ile Thr Lys Trp Ile Phe Asn Trp Lys Lys Asn Asn Trp Lys Ala
            100                 105                 110

Ser Ser Gly Lys Pro Val Lys Asn Gln Asp Leu Trp Ile Ala Leu Asp
            115                 120                 125

Glu Ser Ile Gln Arg His Lys Ile Asn Trp Gln Trp Val Lys Gly His
130                 135                 140

Ala Gly His Arg Glu Asn Glu Ile Cys Asp Glu Leu Ala Lys Lys Gly
145                 150                 155                 160

Ala Glu Asn Pro Thr Leu Glu Asp Met Gly Tyr Phe Glu Glu
                165                 170

<210> SEQ ID NO 27
<211> LENGTH: 161
<212> TYPE: PRT
<213> ORGANISM: Thermus aquaticus

<400> SEQUENCE: 27

Met Ser Leu Pro Leu Lys Arg Val Asp Leu Phe Thr Asp Gly Ala Cys
1               5                   10                  15

Leu Gly Asn Pro Gly Pro Gly Gly Trp Ala Ala Leu Leu Arg Tyr Gly
                20                  25                  30

Ser Gln Glu Lys Leu Leu Ser Gly Gly Glu Pro Cys Thr Thr Asn Asn
            35                  40                  45

Arg Met Glu Leu Arg Ala Ala Leu Glu Gly Leu Leu Ala Leu Arg Glu
50                  55                  60

Pro Cys Gln Val His Leu His Thr Asp Ser Gln Tyr Leu Lys Arg Ala
65                  70                  75                  80

Phe Ala Glu Gly Trp Val Glu Arg Trp Gln Arg Asn Gly Trp Arg Thr
                85                  90                  95

Ala Glu Gly Lys Pro Val Lys Asn Gln Asp Leu Trp Gln Ala Leu Leu
            100                 105                 110

Lys Ala Met Glu Gly His Glu Val Ala Phe His Phe Val Gly Gly His
            115                 120                 125

Ser Gly His Pro Glu Asn Glu Arg Val Asp Arg Glu Ala Arg Arg Gln
130                 135                 140

Ala Lys Ala Gln Pro Gln Val Pro Cys Pro Lys Glu Ala Thr Leu
145                 150                 155                 160

Phe

<210> SEQ ID NO 28
<211> LENGTH: 146

```
<212> TYPE: PRT
<213> ORGANISM: Salmonella enterica

<400> SEQUENCE: 28

Met Leu Lys Gln Val Glu Ile Phe Thr Asp Gly Ser Cys Leu Gly Asn
1               5                   10                  15

Pro Gly Pro Gly Gly Tyr Gly Ala Ile Leu Arg Tyr Arg Gly His Glu
            20                  25                  30

Lys Thr Phe Ser Glu Gly Tyr Thr Leu Thr Thr Asn Asn Arg Met Glu
        35                  40                  45

Leu Met Ala Ala Ile Val Ala Leu Glu Ala Leu Lys Glu His Cys Glu
    50                  55                  60

Val Thr Leu Ser Thr Asp Ser Gln Tyr Val Arg Gln Gly Ile Thr Gln
65                  70                  75                  80

Trp Ile His Asn Trp Lys Lys Arg Gly Trp Lys Thr Ala Glu Lys Lys
                85                  90                  95

Pro Val Lys Asn Val Asp Leu Trp Lys Arg Leu Asp Ala Ala Leu Gly
            100                 105                 110

Gln His Gln Ile Lys Trp Val Trp Val Lys Gly His Ala Gly His Pro
        115                 120                 125

Glu Asn Glu Arg Cys Asp Glu Leu Ala Arg Ala Ala Ala Met Asn Pro
    130                 135                 140

Thr Gln
145

<210> SEQ ID NO 29
<211> LENGTH: 146
<212> TYPE: PRT
<213> ORGANISM: Agrobacterium tumefaciens

<400> SEQUENCE: 29

Met Lys His Val Asp Ile Phe Thr Asp Gly Ala Cys Ser Gly Asn Pro
1               5                   10                  15

Gly Pro Gly Gly Trp Gly Ala Val Leu Arg Tyr Gly Glu Thr Glu Lys
            20                  25                  30

Glu Leu Ser Gly Gly Glu Ala Asp Thr Thr Asn Asn Arg Met Glu Leu
        35                  40                  45

Leu Ala Ala Ile Ser Ala Leu Asn Ala Leu Lys Ser Pro Cys Glu Val
    50                  55                  60

Asp Leu Tyr Thr Asp Ser Ala Tyr Val Lys Asp Gly Ile Thr Lys Trp
65                  70                  75                  80

Ile Phe Gly Trp Lys Lys Lys Gly Trp Lys Thr Ala Asp Asn Lys Pro
                85                  90                  95

Val Lys Asn Val Glu Leu Trp Gln Ala Leu Glu Ala Ala Gln Glu Arg
            100                 105                 110

His Lys Val Thr Leu His Trp Val Lys Gly His Ala Gly His Pro Glu
        115                 120                 125

Asn Glu Arg Ala Asp Glu Leu Ala Arg Lys Gly Met Glu Pro Phe Lys
    130                 135                 140

Arg Arg
145
```